(12) United States Patent
Mach et al.

(10) Patent No.: US 8,722,014 B2
(45) Date of Patent: May 13, 2014

(54) 1 H-[1, 2, 3] TRIAZOLE SUBSTITUTED AMINO ACIDS AND USES THEREOF

(75) Inventors: Robert H. Mach, Eureka, MO (US); Jonathan McConathy, St. Louis, MO (US)

(73) Assignee: Washington University, Saint Louis, MO (US)

( * ) Notice: Subject to any disclaimer, the term of this patent is extended or adjusted under 35 U.S.C. 154(b) by 230 days.

(21) Appl. No.: 12/772,760

(22) Filed: May 3, 2010

(65) Prior Publication Data
US 2010/0278732 A1 Nov. 4, 2010

Related U.S. Application Data

(60) Provisional application No. 61/174,496, filed on May 1, 2009.

(51) Int. Cl.
A61K 49/00 (2006.01)

(52) U.S. Cl.
USPC .......................... 424/9.1; 424/1.89; 548/2.55

(58) Field of Classification Search
None
See application file for complete search history.

(56) References Cited

U.S. PATENT DOCUMENTS

| | | | |
|---|---|---|---|
| 6,964,975 B2 | 11/2005 | Ueno et al. | |
| 7,186,734 B2 | 3/2007 | Maynard et al. | |
| 7,468,371 B2 | 12/2008 | Arnold et al. | |
| 2005/0192458 A1 | 9/2005 | Goodman et al. | |
| 2006/0127306 A1* | 6/2006 | Mertens | 424/1.11 |
| 2007/0081941 A1* | 4/2007 | Mertens | 424/1.11 |

FOREIGN PATENT DOCUMENTS

| | | | |
|---|---|---|---|
| CA | 2667395 A1 * | 5/2008 | |
| WO | 97/05872 | 2/1997 | |
| WO | WO 2004071505 A2 * | 8/2004 | |
| WO | WO 2006067376 A2 * | 6/2006 | |

OTHER PUBLICATIONS

Ikeda et al. Protein Engin. 2003, 16, 699-706.*
Kaira et al. Clin. Cancer Re, 2007, 13, 6369-6378.*
Sirion et al. Tetrahedron Lett. 2007, 3953-3957.*
Bejot et al. Angew. Chem. Int. Ed. 2009, 48, 586-589.*
Gazzola, G.C., et al., Anal. Biochem. 115:368-74, 1981.
Glaser, M. and Arstad, E., Bioconjug. Chem. 18:989-93, 2007.
La Regina, M.C., et al., Lab. Animals. 34:265-71, 2000.
Becherer, A,Szabo, M,Karanikas, G,Wunderbaldinger, P,Angelberger, P,Raderer, M,Kurtaran, A,Dudczak, R; Kletter, K. Imaging of advanced neuroendocrine tumors with 18F-FDOPA PET. J Nucl Med 2004; 45: 1161-7.
Chen, W,Silverman, DH,Delaloye, S,Czernin, J,Kamdar, N,Pope, W,Satyamurthy, N,Schiepers, C; Cloughesy, T. 18F-FDOPA PET imaging of brain tumors: comparison study with 18F-FDG PET and evaluation of diagnostic accuracy. J Nucl Med 2006; 47: 904-11.
Christensen, H.N., et al., "The use of N-methylation to direct route of mediated transport of amino acids," J. Biol. Chem. 240: 3609-3616, 1965.
Closs, EI. Expression, regulation and function of carrier proteins for cationic amino acids. Curr Opin Nephrol Hypertens 2002; 11: 99-107.
Closs, EI,Boissel, JP,Habermeier, A; Rotmann, A. Structure and function of cationic amino acid transporters (CATs). J Membr Biol 2006; 213: 67-77.
Demko, ZP; Sharpless, KB. An intramolecular [2+3] cycloaddition route to fused 5-heterosubstituted tetrazoles. Org Lett 2001; 3: 4091-4.
Esseghir, S,Reis-Filho, JS,Kennedy, A,James, M,O'Hare, MJ,Jeffery, R,Poulsom, R; Isacke, CM. Identification of transmembrane proteins as potential prognostic markers and therapeutic targets in breast cancer by a screen for signal sequence encoding transcripts. J Pathol 2006; 210: 420-30.
Fuchs, BC; Bode, BP. Amino acid transporters ASCT2 and LAT1 in cancer: partners in crime? Semin Cancer Biol 2005; 15: 254-66.
Fuchs, BC,Finger, RE,Onan, MC; Bode, BP. ASCT2 silencing regulates mammalian target-of-rapamycin growth and survival signaling in human hepatoma cells. Am J Physiol Cell Physiol 2007; 293: C55-63.
Furesz et al. "Two cationic amino acid transport systems in human placental basal plasma membranes," Am J Physiol Cell Physiol.1991; 261: C246-C252.
Gajewski M, Seaver BandEsslinger CS. Design, synthesis, and biological activity of novel triazole amino acids used to probe binding interactions between ligand and neutral amino acid transport protein SN1. Bioorg Med Chem Lett 2007;17:4163-6.
Jager, PL,Vaalburg, W,Pruim, J,de Vries, EG,Langen, KJ; Piers, DA. Radiolabeled amino acids: basic aspects and clinical applications in oncology. J Nucl Med 2001; 42: 432-45.
Langen, KJ,Pauleit, D; Coenen, HH. 3-[123I]Iodo-alpha-methyl-L-tyrosine: uptake mechanisms and clinical applications. Nucl Med Biol 2002; 29: 625-31.
Langen, KJ,Hamacher, K,Weckesser, M,Floeth, F,Stoffels, G,Bauer, D,Coenen, HH; Pauleit, D. O-(2-[18F]fluoroethyl)-L-tyrosine: uptake mechanisms and clinical applications. Nucl Med Biol 2006; 33: 287-94.
Langen, KJ,Hamacher, K,Bauer, D,Broer, S,Pauleit, D,Herzog, H,Floeth, F,Zilles, K; Coenen, HH. Preferred stereoselective transport of the D-isomer of cis-4-[18F]fluoro-proline at the blood-brain barrier. J Cereb Blood Flow Metab 2005; 25: 607-16.
Makrides, V,Bauer, R,Weber, W,Wester, HJ,Fischer, S,Hinz, R,Huggel, K,Opfermann, Herzau M, Ganapathy V, Verrey F, Brust P, Preferred transport of O-(2-[18F]fluoroethyl)-D-tyrosine (D-FET) into the porcine brain. Brain Res 2007; 1147: 25-33.

(Continued)

Primary Examiner — Michael G Hartley
Assistant Examiner — Sean R Donohue
(74) Attorney, Agent, or Firm — Saul L Zackson; Zackson Law LLC

(57) ABSTRACT

Tracers for cationic amino acid transport systems and methods of synthesis are disclosed, including compounds comprising a 1H-[1,2,3]triazole moiety. Further disclosed are uses of the analogues, including in vivo imaging of tumors by Positron emission tomography (PET) or Single Photon Emission Computed Tomography (SPECT).

15 Claims, 13 Drawing Sheets

(56) References Cited

OTHER PUBLICATIONS

Martarello, L,McConathy, J,Camp, VM,Malveaux, EJ,Simpson, NE,Simpson, CP,Olson, JJ,Bowers, GD; Goodman, MM. Synthesis of syn- and anti-1-amino-3-[18F]fluoromethyl-cyclobutane-1-carboxylic acid (FMACBC), potential PET ligands for tumor detection. J Med Chem 2002; 45: 2250-9.

McConathy, J,Martarello, L,Malveaux, EJ,Camp, VM,Simpson, NE,Simpson, CP,Bowers, GD,Olson, JJ; Goodman, MM. Radiolabeled amino acids for tumor imaging with PET: radiosynthesis and biological evaluation of 2-amino-3-[18F]fluoro-2-methylpropanoic acid and 3-[18F]fluoro-2-methyl-2-(methylamino)propanoic acid. J Med Chem 2002; 45: 2240-9.

McConathy, J,Martarello, L,Malveaux, EJ,Camp, VM,Simpson, NE,Simpson, CP,Bowers, GD,Zhang, Z,Olson, JJ; Goodman, MM. Synthesis and evaluation of 2-amino-4-[18F]fluoro-2-methylbutanoic acid (FAMB): relationship of amino acid transport to tumor imaging properties of branched fluorinated amino acids. Nucl Med Biol 2003; 30: 477-90.

McConathy, J; Goodman, MM. Non-natural amino acids for tumor imaging using positron emission tomography and single photon emission computed tomography. Cancer Metastasis Rev 2008; 27: 555-73.

Mindt TL, Struthers H, Brans L, et al. "Click to chelate": synthesis and installation of metal chelates into biomolecules in a single step. J Am Chem Soc 2006;128:15096-7.

Montravers, F,Grahek, D,Kerrou, K,Ruszniewski, P,de Beco, V,Aide, N,Gutman, F,Grange, JD,Lotz, JP; Talbot, JN. Can fluorodihydroxyphenylalanine PET replace somatostatin receptor scintigraphy in patients with digestive endocrine tumors? J Nucl Med 2006; 47: 1455-62.

Nawashiro, H., et al. "L-type amino acid transporter 1 as a potential molecular target in human astrocytic tumors," Int. J. Cancer 119: 484-492, 2006.

Oka, S,Hattori, R,Kurosaki, F,Toyama, M,Williams, LA,Yu, W,Votaw, JR,Yoshida, Y,Goodman, MM; Ito, O. A preliminary study of anti-1-amino-3-18F-fluorocyclobutyl-1-carboxylic acid for the detection of prostate cancer. J Nucl Med 2007; 48: 46-55.

Palacin, M., et al., "Molecular biology of mammalian plasma membrane amino acid transporters," Physiol. Rev. 78: 969-1054, 1998.

Schuster, DM,Votaw, JR,Nieh, PT,Yu, W,Nye, JA,Master, V,Bowman, FD,Issa, MM; Goodman, MM. Initial experience with the radiotracer anti-1-amino-3-18F-fluorocyclobutane-1-carboxylic acid with PET/CT in prostate carcinoma. J Nucl Med 2007; 48: 56-63.

Shotwell, M.A., et al. "The regulation of neutral amino acid transport in mammalian cells," Biochem. Biophys. Acta. 737: 267-284, 1983.

Shoup, TM,Olson, J,Hoffman, JM,Votaw, J,Eshima, D,Eshima, L,Camp, VM,Stabin, M,Votaw, D; Goodman, MM Synthesis and evaluation of [18F]1-amino-3-fluorocyclobutane-1-carboxylic acid to image brain tumors. J Nucl Med 1999; 40: 331-8.

Singhal, T, Narayanan, TK, Jain, V, Mukherjee, J; Mantil, J. [11C]-L-methionine positron emission tomography in the clinical management of cerebral gliomas. Mol Imaging Biol 2008; 10: 1-18.

Yu, W,McConathy, J,Olson, J,Camp, VM; Goodman, MM. Facile Stereospecific Synthesis and Biological Evaluation of (S)- and (R)-2-Amino-2-methyl-4-[123I]iodo-3-(E)-butenoic Acid for Brain Tumor Imaging with Single Photon Emission Computerized Tomography. J Med Chem 2007; 50: 6718-21.

Yu WP, McConathy J, Williams L, et al. Synthesis, Radiolabeling, and Biological Evaluation of (R)- and (S)-2-Amino-3-[F-18]Fluoro-2-Methylpropanoic Acid (FAMP) and (R)- and (S)-3[F-18]Fluoro-2-Methyl-2-N-(Methylamino)propanoic Acid (NMeFAMP) as Potential PET Radioligands for Imaging Brain Tumors. Journal of Medicinal Chemistry 2010;53:876-86.

Bergmann et al. 3-O-Methyl-6-18F-Fluoro-L-Dopa, a New Tumor Imaging Agent: Investigation of Transport Mechanism In Vitro. J. Nucl Med 2004; 45: 2116-22.

Glaser M et al. "Click Labeling" with 2-[18F]Fluoroethylazide for Positron Emission Tomography. Bioconjugate Chem., 2007, 18 (3), 989-993.

Ikeda Y et al. Synthesis of a novel histidine analogue and its efficient incorporation into a protein in vivo. Protein Engineering vol. 16 No. 9 pp. 699±706, 2003.

Smith G et al. Design, Synthesis, and Biological Characterization of a Caspase 3/7 Selective Isatin Labeled with 2-[18F]fluoroethylazide. J. Med. Chem., 2008, 51 (24), 8057-8067.

\* cited by examiner

1H-[1, 2, 3] TRIAZOLE SUBSTITUTED AMINO ACIDS AND USES THEREOF

STATEMENT REGARDING FEDERALLY SPONSORED RESEARCH OR DEVELOPMENT

This invention was made with the support of Grant NS48056 from the National Institutes of Health. The government of the United States of America has certain rights in this work.

PRIORITY STATEMENT

This application claims the benefit of and priority to U.S. Provisional Application No. 61/174,496, filed on May 1, 2009, which is incorporated herein by reference in its entirety.

BACKGROUND

Radiolabeled amino acids are an important class of tumor imaging agents that target the increased rates of amino acid transport that occur in many types of tumor cells. A number of radiolabeled amino acids including L-[$^{11}$C]methionine, (2-[$^{18}$F]fluoroethyl)-L-tyrosine (FET), 6-[$^{18}$F]fluoro-3,4-dihydroxy-L-phenylalanine (FDOPA), 3-[$^{123}$I]iodo-a-methyl-L-tyrosine (IMT) have proven utility for imaging gliomas in human patients. (Singhal, T, et al. Mol. Imaging. Biol. 10:1-18, 2008; Langen, K. J., et al. Nucl. Med. Bio 33: 287-294, 2006; Chen, W., et al. J. Nuc. Med. 47: 904-911, 2006; Langen, K. J., et al. Nucl. Med. Biol. 29: 625-631, 2006; McConathy, J., et al. Cancer Metastasis Rev. 27: 555-573, 2008). These tracers have improved sensitivity and specificity relative to 2-[$^{18}$F]fluoro-2-deoxy-D-glucose (FDG) for detecting brain gliomas, particularly in the setting of recurrence after treatment. Radiolabeled amino acids also can increase the diagnostic yield of stereotactic biopsy and provide better delineation of tumor volumes for treatment planning than contrast enhanced magnetic resonance (MR) imaging alone. Radiolabeled amino acids may also be useful for monitoring response to therapy and differentiating low grade from high grade gliomas. Amino acids may also be useful in imaging tumors outside of the brain. For example, [$^{18}$F]FDOPA appears to be useful for imaging carcinoid and other neuroendocrine tumors, and anti-3-[$^{18}$F]fluoro-1-amino-1-cyclobutane carboxylic acid (FACBC) has shown promising preliminary results for imaging prostate cancer. (Becherer, A., et al. J. Nucl. Med. 45: 1161-1167, 2004; Montravers, F., et al. J. Nucl. Med. 47: 1455-1462, 2006; Schuster, D. M., et al. J. Nucl. Med. 48: 56-63, 2007; Oka, S., et al. J. Nucl. Med. 48: 46-55, 2007).

Amino acids enter cells via membrane-associated carrier transport proteins. Over 20 mammalian amino acid transport systems have been described with varying substrate specificities, pH dependence, sodium dependence and regulatory mechanisms. A number of amino acid transport subtypes including L-type amino acid transporter 1 (LAT1) and amino acid transporter type 2 (ASCT2) have been shown to be upregulated in various human tumors including breast cancers and gliomas, and their presence may have prognostic significance. (Fuchs, B. C., et al. Am. J. Physiol. Cell. Physiol. 293: C55-C63, 2007; Fuchs, B. C., et al. Semin. Cancer Biol. 15: 254-266; Esseghir, S., et al. J. Pathol. 210: 420-430, 2006; Nawashiro, H., et al. Int. J. Cancer 119: 484-492, 2006). The leucine-preferring amino acid transport system (system L) and to a lesser extent the alanine-preferring amnion acid transport system (system A) have been the major focus of radiolabeled amino acid development for positron emission tomography (PET) and single photon computed tomography (SPECT). However, health care professionals are in need of radiolabeled amino acids suitable for PET and SPECT that target amino acid transport systems other than system L and system A, such as cationic amino acid transport.

SUMMARY

The present inventors have developed a series of compounds which can be used as radiolabels for diagnostic imaging, in particular positron emission tomography (PET) imaging of tumors in a mammal.

In some embodiments, the present teachings disclose a radiolabeled 1H-[1,2,3]triazole substituted amino acid or salt thereof of structure

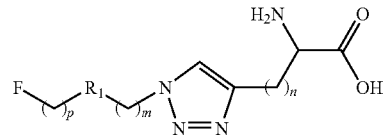

wherein $R_1$ can be $CH_2$ or O, n can be an integer from 0 to 3, m can be an integer from 0 to 1, and p can be an integer from 0 to 1.

In additional embodiments of the present teachings, the inventors disclose a radiolabeled 1H-[1,2,3]triazole substituted amino acid or salt thereof of structure

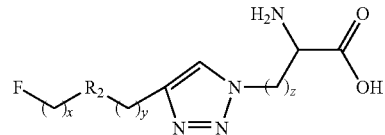

wherein $R_2$ can be $CH_2$ or O, z can be an integer from 0 to 3, y can be an integer from 0 to 1, and x an integer from 0 to 2.

In additional embodiments of the present teachings, the inventors disclose methods of imaging a tumor in mammal such as human. These methods comprise administering to the mammal a radiolabeled 1H-[1,2,3]triazole substituted amino acid or salt thereof of structure

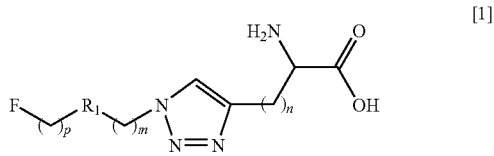

[1]

wherein $R_1$ can be $CH_2$ or O, n can be an integer from 0 to 3, m can be an integer from 0 to 1, and p can be an integer from 0 to 1, and subjecting the mammal to PET scanning.

In additional embodiments of the present teachings, the inventors disclose methods of imaging a tumor in mammal such as human. These methods comprise administering to the mammal a radiolabeled 1H-[1,2,3]triazole substituted amino acid or salt thereof of structure

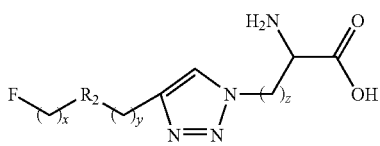

wherein $R_2$ can be $CH_2$ or O, z can be an integer from 0 to 3, y can be an integer from 0 to 1, and x can be an integer from 0 to 2, and subjecting the mammal to PET scanning.

In some embodiments, a compound of the present teachings can be a radiolabeled 1H-[1,2,3]triazole substituted amino acid or salt thereof as disclosed herein, wherein $R_1$ can be $CH_2$, n can be from 1 to 3, m can be 0, p can be 1, and F can be [$^{18}$F. [1]

In some embodiments, a compound of the present teachings can be a radiolabeled 1H-[1,2,3]triazole substituted amino acid or salt thereof as disclosed herein, wherein $R_1$ can be $CH_2$, n can be 1, m can be 0, p can be 1, and F can be an $^{18}$F. [1]

In some embodiments, a compound of the present teachings can be a radiolabeled 1H-[1,2,3]triazole substituted amino acid or salt thereof as disclosed herein, wherein $R_1$ can be $CH_2$, n can be 2, m can be 0, p can be 1, and F can be an $^{18}$F. [1]

In some embodiments, a compound of the present teachings can be a radiolabeled 1H-[1,2,3]triazole substituted amino acid or salt thereof as disclosed herein, wherein $R_1$ can be $CH_2$, n can be 3, m can be 0, p can be 1, and F can be an $^{18}$F. [1]

In various aspects of the above embodiments, a radiolabeled 1H-[1,2,3]triazole substituted amino acid or salt thereof can include particular molecular species, such as [1]

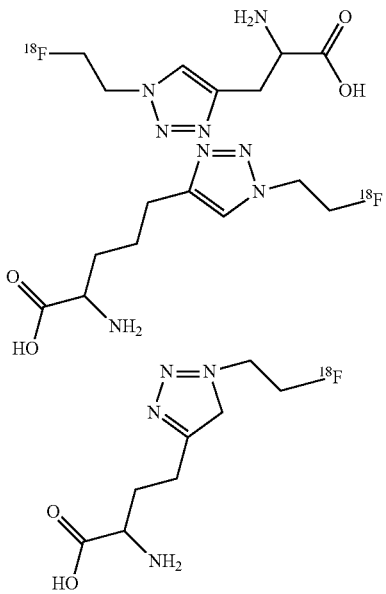

In some embodiments, a compound of the present teachings can be a radiolabeled 1H-[1,2,3]triazole substituted amino acid or salt thereof as disclosed herein, wherein $R_2$ can be O, z can be 1 to 3, y can be 1, x can be 2, and the F can be an $^{18}$F. [2]

In some embodiments, a compound of the present teachings can be a radiolabeled 1H-[1,2,3]triazole substituted amino acid or salt thereof as disclosed herein, wherein $R_2$ can be O, z can be 1, y can be 1, x can be 2, and the F can be an $^{18}$F. [2]

In some embodiments, a compound of the present teachings can be a radiolabeled 1H-[1,2,3]triazole substituted amino acid or salt thereof as disclosed herein, wherein $R_2$ can be O, z can be 2, y can be 1, x can be 2, and the F can be an $^{18}$F. [2]

In some embodiments, a compound of the present teachings can be a radiolabeled 1H-[1,2,3]triazole substituted amino acid or salt thereof as disclosed herein, wherein $R_2$ can be O, z can be 3, y can be 1, x can be 2, and the F can be an $^{18}$F. [2]

In various aspects of the above embodiments, a radiolabeled 1H-[1,2,3]triazole substituted amino acid or salt thereof can include particular molecular species, such as

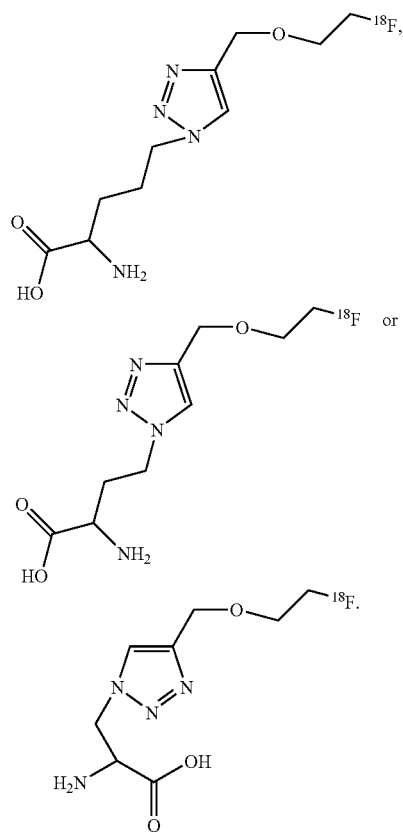

The present teachings include the following aspects:
1. A radiolabeled 1H-[1,2,3]triazole substituted amino acid or salt thereof of structure

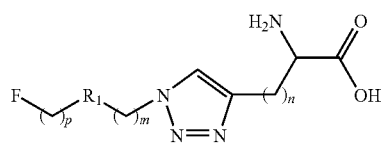

wherein $R_1$ is $CH_2$ or O, n is an integer from 0 to 3, m is an integer from 0 to 1, and p is an integer from 0 to 1.

2. A radiolabeled 1H-[1,2,3]triazole substituted amino acid or salt thereof in accordance with aspect 1, wherein the F is an $^{18}$F.

3. A radiolabeled 1H-[1,2,3]triazole substituted amino acid or salt thereof in accordance with aspect 1, wherein $R_1$ is $CH_2$, n is from 1 to 3, m is 0, p is 1, and F is an $^{18}F$ 4. A radiolabeled 1H-[1,2,3]triazole substituted amino acid or salt thereof in accordance with aspect 1, wherein $R_1$ is $CH_2$, n is 1, m is 0, p is 1, and F is an $^{18}F$.

5. A radiolabeled 1H-[1,2,3]triazole substituted amino acid or salt thereof in accordance with aspect 1, wherein $R_1$ is $CH_2$, n is 2, m is 0, p is 1, and F is an $^{18}F$.

6. A radiolabeled 1H-[1,2,3]triazole substituted amino acid or salt thereof in accordance with aspect 1, wherein $R_1$ is $CH_2$, n is 3, m is 0, p is 1, and F is an $^{18}F$.

7. A radiolabeled 1H-[1,2,3]triazole substituted amino acid or salt thereof in accordance with aspect 1, wherein the acid is selected from the group consisting of

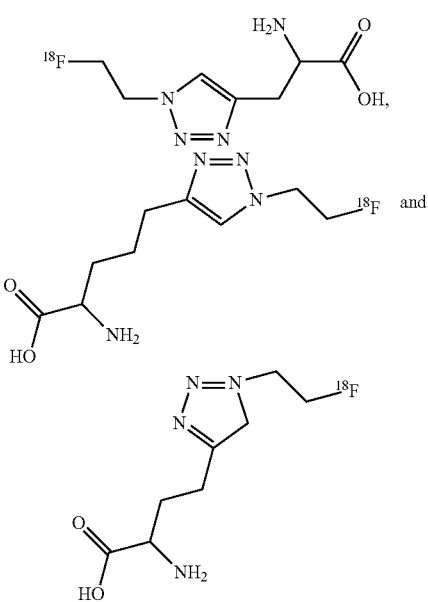

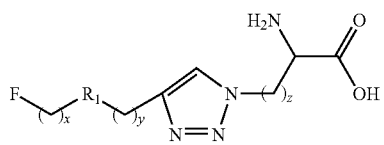

8. A radiolabeled 1H-[1,2,3]triazole substituted amino acid or salt thereof of structure

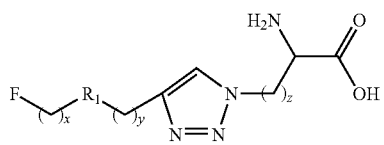

wherein $R_2$ is $CH_2$ or O, z is an integer from 0 to 3, y is an integer from 0 to 1, and x is an integer from 0 to 2.

9. A radiolabeled 1H-[1,2,3]triazole substituted amino acid or salt thereof in accordance with aspect 8, wherein the F is an $^{18}F$.

10. A radiolabeled 1H-[1,2,3]triazole substituted amino acid or salt thereof in accordance with aspect 8, wherein $R_2$ is O, z is 1 to 3, y is 1, x is 2, and the F is an $^{18}F$.

11. A radiolabeled 1H-[1,2,3]triazole substituted amino acid or salt thereof in accordance with aspect 8, wherein $R_2$ is O, z is 1, y is 1, x is 2, and the F is an $^{18}F$.

12. A radiolabeled 1H-[1,2,3]triazole substituted amino acid or salt thereof in accordance with aspect 8, wherein $R_2$ is O, z is 2, y is 1, x is 2, and the F is an $^{18}F$.

13. A radiolabeled 1H-[1,2,3]triazole substituted amino acid or salt thereof in accordance with aspect 8, wherein $R_2$ is O, z is 3, y is 1, x is 2, and the F is an $^{18}F$.

14. A radiolabeled 1H-[1,2,3]triazole substituted amino acid or salt thereof in accordance with aspect 8, wherein the acid is selected from the group consisting of

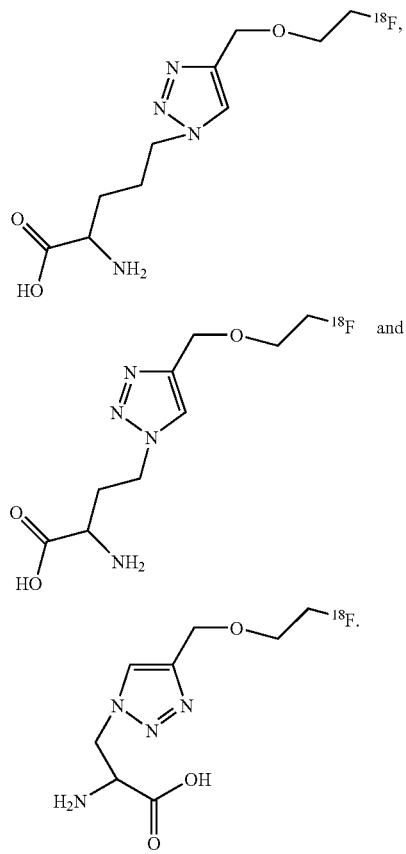

15. A method of imaging a tumor in a mammal, the method comprising:
   administering to the mammal a radiolabeled 1H-[1,2,3]triazole substituted amino acid or salt thereof, of any one of aspects 1-14; and subjecting the mammal to PET scanning.

16. A method of imaging a tumor in a mammal in accordance with aspect 15, wherein the radiolabeled 1H-[1,2,3]triazole substituted amino acid is selected from the group consisting of

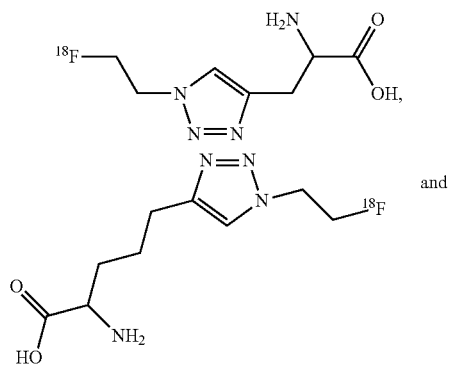

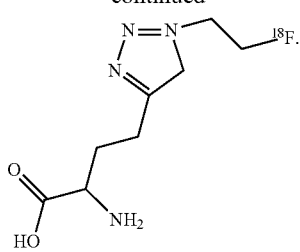

17. A method of imaging a tumor in a mammal in accordance with aspect 15, wherein the radiolabeled 1H-[1,2,3]triazole substituted amino acid is selected from the group consisting of

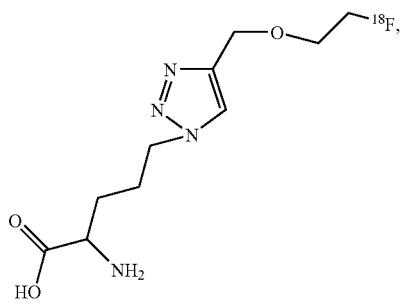

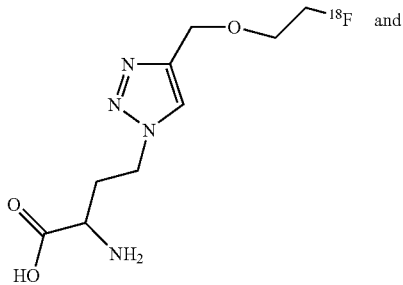

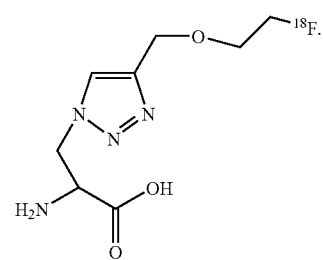

18. A method of synthesizing

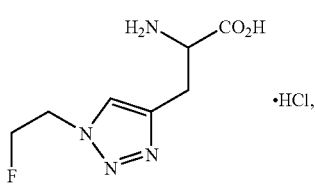

comprising:

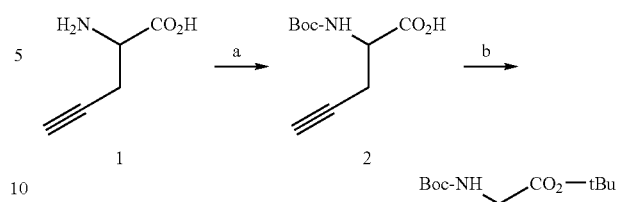

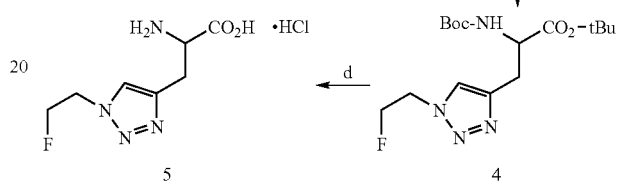

a) contacting compound 1 with 1.5 eq (Boc)$_2$O and 9:1 CH$_3$OH, Et$_3$N to yield compound 2;
b) contacting compound 2 with Cl$_3$CC(=NH)OtBu, and CH$_2$Cl$_2$ to yield compound 3;
c) contacting compound 3 with FCH$_2$CH$_2$N$_3$, CuI, and DMF/THF to yield compound 4;
d) contacting compound 4 with aqueous HCL and EtOH at 60° C.

19. A method of synthesizing

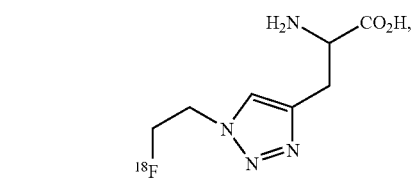

comprising:

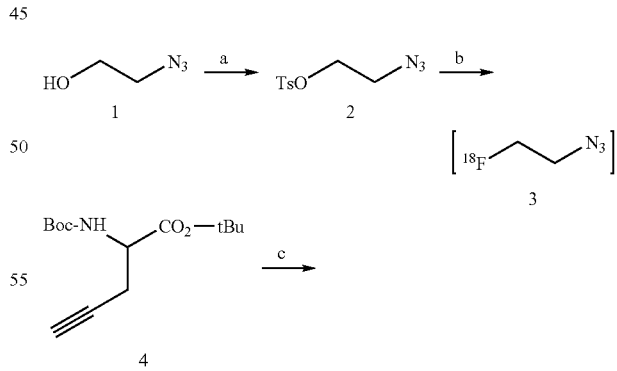

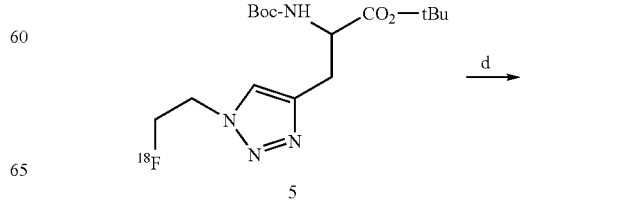

-continued

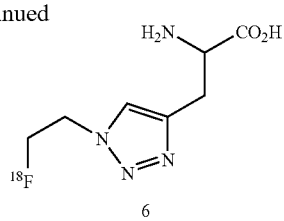

a) contacting compound 1 with 1.5 eq TsCl, Et$_3$N, and CH$_2$Cl$_2$ to yield compound 2;
b) contacting compound 2 with) K[$^{18}$F]F, K$_{222}$, and K$_2$CO$_3$ to yield compound 3;
c) contacting compound 4 with compound 3, Cu(SO$_4$), and sodium L-ascorbate to yield compound 5;
d) contacting compound 5 with aqueous HCL aqueous HCl, and then heating by microwave/

DETAILED DESCRIPTION

Figure 1:
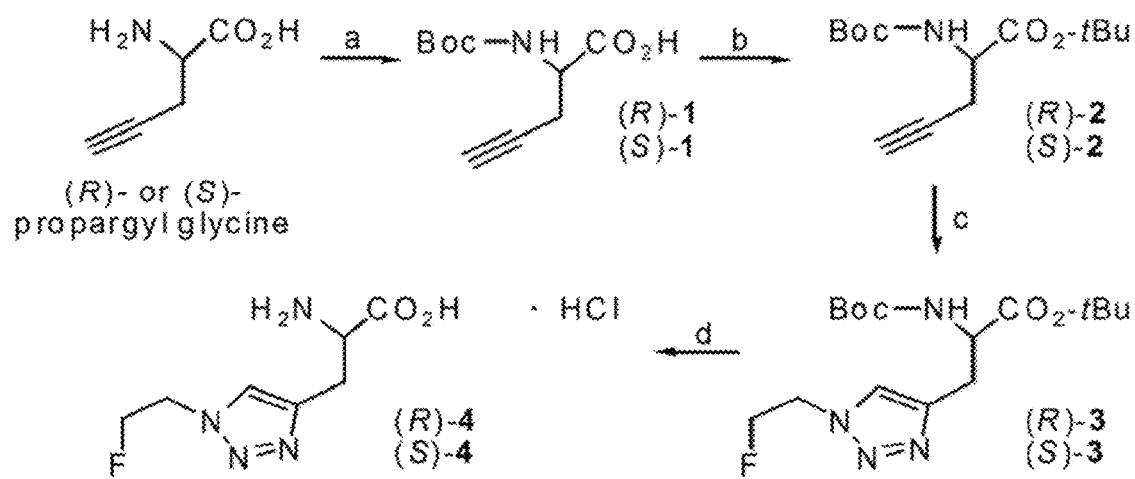
FIG. 1 illustrates the synthesis scheme for (R)-4 and (S)-4.

The present inventors have developed a series of compounds which can be used as tracers for diagnostic imaging, in particular positron emission topography (PET) imaging of a tumor in a mammalian subject such as a human. In some embodiments, a compound can comprise a radioisotrope, such as a positron emitter. Accordingly, a compound of the present teachings can include a radioisotope such as $^{18}$F. In some embodiments, a compound can comprise a radioisotrope, and can be used as a radiotracer for imaging tumors in a human or other mammal using positron emission topography (PET).

Hence, in some aspects, the inventors provides methods of imaging tumors in a human or other animal. These methods comprise administering to the mammal a radiolabeled 1H-[1,2,3]triazole substituted amino acid or salt thereof and subjecting the mammal to PET scanning. In some configurations, the PET scanning can yield an image which can then be interpreted by a medical professional, such as a physician.

Without limitation, a radiolabeled amino acid of the present teachings can be useful in imaging tumors such as, for example, a brain tumor, a carcinoid tumor, or a prostate tumor. Imaging tumors can be useful, for example, for monitoring response to therapy, such as chemotherapy and radiation. Thus, the present radiotracers and methods can be used, for example, by a medical professional to determine if a therapy is effective. In some configurations, tumor imaging using the disclosed compounds as tracers can also be useful for differentiating low grade from high grade gliomas.

In some embodiments, a compound of the present teachings can be a radiolabeled 1H-[1,2,3]triazole substituted amino acid or salt thereof of structure

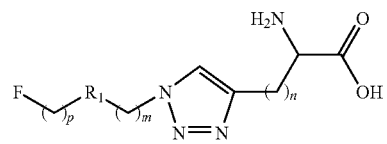

wherein R$_1$ is CH$_2$ or O, n is an integer from 0 to 3, m is an integer from 0 to 1, and p is an integer from 0 to 1.

In additional embodiments, a compound of the present teachings can be a radiolabeled the inventors disclose a radiolabeled 1H-[1,2,3]triazole substituted amino acid or salt thereof of structure

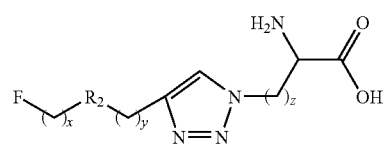

wherein R$_2$ is CH$_2$ or O, z is an integer from 0 to 3, y is an integer from 0 to 1, and x is an integer from 0 to 2.

In additional embodiments of the present teachings, the inventors disclose methods of imaging a tumor in mammal such as human. These methods comprise administering to the mammal a radiolabeled 1H-[1,2,3]triazole substituted amino acid or salt thereof of structure

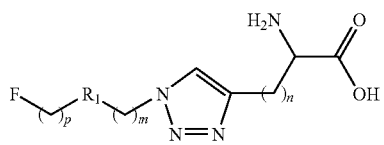

wherein $R_1$ is $CH_2$ or O, n is an integer from 0 to 3, m is an integer from 0 to 1, and p is an integer from 0 to 1, and subjecting the mammal to PET scanning.

In additional embodiments of the present teachings, the inventors disclose methods of imaging a tumor in mammal such as human. These methods comprise administering to the mammal a radiolabeled 1H-[1,2,3]triazole substituted amino acid or salt thereof of structure

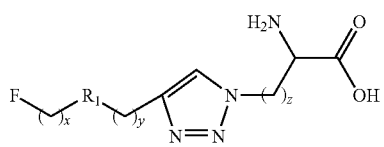

wherein $R_2$ is $CH_2$ or O, z is an integer from 0 to 3, y is an integer from 0 to 1, and x is an integer from 0 to 2.

In some embodiments, a compound of the present teachings is a radiolabeled 1H-[1,2,3]triazole substituted amino acid or salt thereof as disclosed herein, wherein $R_1$ is $CH_2$, n is from 1 to 3, m is 0, p is 1, and F is $^{18}F$. [1]

In some embodiments, a compound of the present teachings is a radiolabeled 1H-[1,2,3]triazole substituted amino acid or salt thereof as disclosed herein, wherein $R_1$ is $CH_2$, n is 1, m is 0, p is 1, and F is an $^{18}F$. [1]

In some embodiments, a compound of the present teachings is a radiolabeled 1H-[1,2,3]triazole substituted amino acid or salt thereof as disclosed herein, wherein $R_1$ is $CH_2$, n is be 2, m is 0, p is 1, and F is an $^{18}F$. [1]

In some embodiments, a compound of the present teachings is a radiolabeled 1H-[1,2,3]triazole substituted amino acid or salt thereof as disclosed herein, wherein $R_1$ is $CH_2$, n is 3, m is 0, p is 1, and F is an $^{18}F$. [1]

In various aspects of the above embodiments, a radiolabeled 1H-[1,2,3]triazole substituted amino acid or salt thereof includes particular molecular species, such as [1]

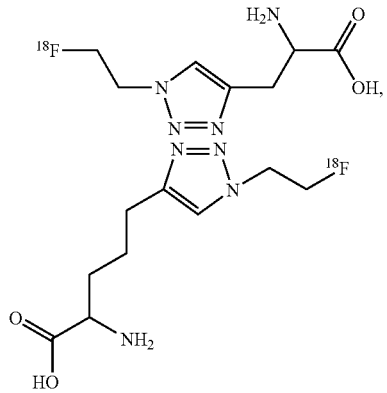

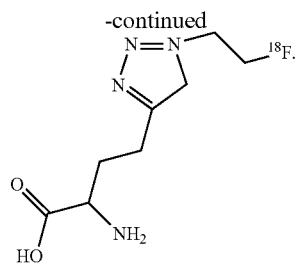

In some embodiments, a compound of the present teachings is a radiolabeled 1H-[1,2,3]triazole substituted amino acid or salt thereof as disclosed herein, wherein $R_2$ is O, z is 1 to 3, y is 1, x is 2, and the F is an $^{18}F$. [2]

In some embodiments, a compound of the present teachings is a radiolabeled 1H-[1,2,3]triazole substituted amino acid or salt thereof as disclosed herein, wherein $R_2$ is O, z is 1, y is 1, x is 2, and the F is an $^{18}F$. [2]

In some embodiments, a compound of the present teachings is a radiolabeled 1H-[1,2,3]triazole substituted amino acid or salt thereof as disclosed herein, wherein $R_2$ is O, z is 2, y is 1, x is 2, and the F is an $^{18}F$. [2]

In some embodiments, a compound of the present teachings is a radiolabeled 1H-[1,2,3]triazole substituted amino acid or salt thereof as disclosed herein, wherein $R_2$ is O, z is 3, y is 1, x is 2, and the F is an $^{18}F$. [2]

In various aspects of the above embodiments, a radiolabeled 1H-[1,2,3]triazole substituted amino acid or salt thereof includes particular molecular species, such as

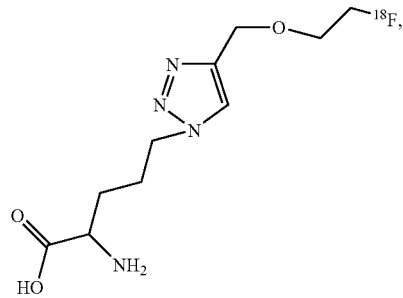

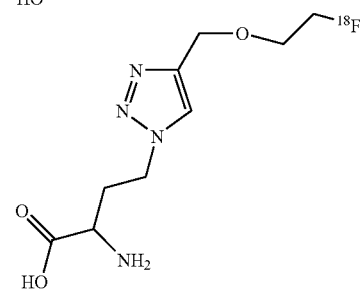

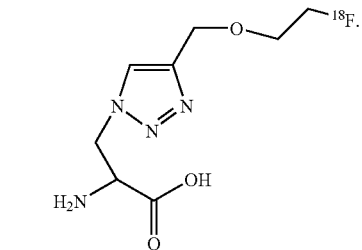

In various aspects of the embodiments, methods for synthesis of the compounds disclosed herein are provided. In particular aspects, methods of synthesis of radiolabeled 1H-[1,2,3]triazole substituted amino acids or salts thereof are provided. In further aspects, methods for synthesis of radiolabeled 1H-[1,2,3]triazole substituted amino acid precursors are also provided.

EXAMPLES

The following examples are illustrative of the various embodiments of the present teachings. The examples are not intended to limit the scope of the claims. The methods described herein utilize laboratory techniques well known to skilled artisans, and guidance can be found in laboratory manuals and textbooks such as Sambrook, J., et al., Molecular Cloning: A Laboratory Manual, 3rd ed. Cold Spring Harbor Laboratory Press, Cold Spring Harbor, N.Y., 2001; Spector, D. L. et al., Cells: A Laboratory Manual, Cold Spring Harbor Laboratory Press, Cold Spring Harbor, N.Y., 1998; and Harlow, E., Using Antibodies: A Laboratory Manual, Cold Spring Harbor Laboratory Press, Cold Spring Harbor, N.Y., 1999; Hedrickson et al., Organic Chemistry 3rd edition, McGraw Hill, N.Y., 1970; Carruthers, W., and Coldham, I., Modern Methods of Organic Synthesis (4th Edition), Cambridge University Press, Cambridge, U.K., 2004; Curati, W. L., Imaging in Oncology, Cambridge University Press, Cambridge, U.K., 1998; Welch, M. J., and Redvanly, C. S., eds. Handbook of Radiopharmaceuticals: Radiochemistry and Applications, J. Wiley, New York, 2003.

In the experiments described herein, all reagents, reactions and materials were purchased from commercial suppliers and used without further purification unless otherwise stated. Chemicals were purchased from Aldrich Chemicals Co. (Milwaukee, Wis. USA) and Sigma Chemical Co. (St. Louis, Mo. USA) unless otherwise specified, and solvents were purchased from Aldrich Chemicals and Fisher Scientific Products (Pittsburgh, Pa. USA). Flash chromatography was conducted using Merck Kieselgel silica gel 60 (230-400 mesh). Thin-layer chromatography (TLC) analyses were performed with 250 μm UV254 silica gel backing on glass plates (Aldrich Chemicals Co.). The TLC plates were visualized with ninhydrin and/or phosphomolybdic acid stains. Alumina and C-18 SepPaks were purchased from Waters, Inc. (Milford, Mass. USA). Ion-retardation resin (AG 11A8 50-100 mesh) was purchased from BioRad. (Hercules, Calif., USA).

Melting points were measured in capillary tubes and are uncorrected. Hydrogen-1 Nuclear Magnetic Resonance ($^1$H NMR) spectra were recorded on a Varian 300 MHz spectrometer, and chemical shifts (d values) were reported as parts per million (ppm) downfield from tetramethylsilane (TMS), and coupling values in Hertz (Hz). Elemental analyses were performed by Atlantic Microlabs, Inc. (Norcross, Ga. USA) and were within ±0.4% of the theoretical values. The phrase "usual work up" refers to removal of residual water with anhydrous magnesium sulfate followed by rotary evaporation.

Example 1

This example illustrates synthesis of (R)-2-[N-(tert-butoxycarbonyl)amino]-4-pentynoic acid (compound (R)-1) and (S)-2-[N-(tert-butoxycarbonyl)amino]-4-pentynoic acid (compound (S)-1) (FIG. 1).

To synthesize compound (R)-1, 500 mg portion of (R)-propargyl glycine (4.42 mmol) was suspended in a solution of 18 mL methanol and 1.8 mL of triethylamine, and a 1.8 mL portion of water was added to provide a homogeneous solution. A 2.0 equivalent portion of di-tert-butyl dicarbonate (1.89 g) was added, and the reaction mix was stirred at room temperature overnight. The reaction mix was concentrated under reduced pressure, and the residue was partitioned between 40 mL of ethyl acetate and 30 mL of 0.2M aqueous hydrochloric acid. The organic phase was retained, and the aqueous phase was extracted with 2×20 mL of ethyl acetate. The combined organic extracts were washed with 2×30 mL of water followed by usual work up to provide a colorless thick oil (1.06 g, 112%) suitable for use in the next step without further purification. The $^1$H NMR spectra (CDCl$_3$) of the product was: 1.47 (9H, s), 2.09 (1H, t, J=2.9), 2.75-2.86 (2H, broad m), 4.49-4.57 (1H, m), 5.34 (1H, d, J=8.1).

To synthesize compound (S)-1, a 200 mg portion of (S)-propargyl glycine provided 430 mg of (S)-1 (110%) suitable for use in the next step without further purification. The $^1$H NMR spectrum of (S)-1 was the same as for (R)-1.

Example 2

This examples illustrates synthesis of (R)-2-[N-(tert-butoxycarbonyl)amino]-4-pentynoic acid tert-butyl ester (compound (R)-2) and (S)-2-[N-(tert-butoxycarbonyl)amino]-4-pentynoic acid tert-butyl ester (compound (S)-2) (FIG. 1).

To synthesize compound (R)-2, a 640 mg portion of the N-Boc acid (R)-1 (2.99 mmol) was dissolved in 4 mL of anhydrous dichloromethane. A 3.0 equivalent portion of tert-butyl-2,2,2-trichloroacetimidate (1.96 g) was added, and the reaction mix was stirred at room temperature overnight. The supernatant containing the product was isolated, and the remaining solid byproducts were washed with 4×5 mL portions of 3:97 ethyl acetate:hexane. The supernatant and the washes were combined and concentrated under reduced pressure. Purification by silica gel flash chromatography (1:9 ethyl acetate:hexane) provided (R)-2 as a white solid (685 mg, 88%). The $^1$H NMR spectra (CDCl$_3$) of the product was: 1.45 (9H, s), 1.49 (9H, s), 2.02 (1H, t, J=2.7), 2.69-2.71 (2H, m), 4.31-4.37 (1H, m), 5.35 (1H, d, J=7.5). Anal. (C$_{14}$H$_{23}$NO$_4$) C, H, N.

To synthesize compound (S)-2, a 350 mg portion of (S)-1 provided 339 mg (77%) of (S)-2 as a white solid. The $^1$H NMR spectrum of (S)-2 was the same as for (R)-2. Anal. (C$_{14}$H$_{23}$NO$_4$) C, H, N.

Example 3

This example illustrates synthesis of (R)-2-[N-(tert-butoxycarbonyl)amino]-3-[1-(2-fluoroethyl)-1H-[1,2,3]triazol-4-yl]propanoic acid tert-butyl ester (compound (R)-3) and (S)-2-[N-(tert-butoxycarbonyl)amino]-3-[1-(2-fluoroethyl)-1H-[1,2,3]triazol-4-yl]propanoic acid tert-butyl ester (compound (S)-3) (FIG. 1).

To synthesize compound (R)-3, the reaction was performed based on conditions reported in Glaser et al., Bioconjug. Chem. 18: 989-993, 2007.

A 1.07 equivalent portion of 1-(4-methylbenzenesulfonate)-2-fluoroethanol (200 mg, 0.917 mmol) in 4 mL of N,N-dimethylformamide was stirred with a suspension of 3.2 equivalent of sodium azide (179 mg) at room temperature. After 48 hours, the solution was filtered, and the crude 1-azido-2-fluoroethane was used immediately in the next step without further purification.

In a separate flask, a 5.4 equivalent portion of copper (I) iodide (873 mg) was suspended in 2 mL of methanol under an argon atmosphere with vigorous stirring. In rapid succession, a 1.0 equivalent portion of (R)-2 (229 mg, 0.85 mmol) in 1 mL of methanol, the crude 1-azido-2-fluoroethane in approximately 4 mL of N,N-dimethylformamide and 5.4 equivalent of triethylamine (640 mL) were added. The reaction mix was stirred overnight at room temperature. The reaction mix was then partitioned between 20 mL of saturated aqueous sodium bicarbonate and 20 mL of diethyl ether. The organic layer was retained, and the aqueous layer was extracted with additional 2×20 mL volumes of diethyl ether. The combined organic layers were washed with 3×20 mL of water followed by usual work up. Purification by silica gel flash chromatography (1:1 ethyl acetate) provided (R)-3 as a colorless oil (239 mg, 78%). The $^1$H NMR spectra (CDCl$_3$) of the product was: 1.42 (9H, s), 1.43 (9H, s), 3.22 (2H, d, J=5.4), 4.45-4.51 (1H, m), 4.59-4.62 (1H, m), 4.67-4.72 (2H, m), 4.84-4.87 (1H, m), 5.43 (1H, broad d, J=8.1), 7.50 (1H, s). Anal. (C$_{16}$H$_{27}$FN$_4$O$_4$).

To synthesize (S)-3, the reaction was performed as for the compound (R)-3 with slightly higher excesses of reagents (i.e. 1.5 eq 1-(4-methylbenzenesulfonate)-2-fluoroethanol, 4.5 eq of sodium azide, 6.4 eq of copper (I) iodide, 6.4 eq of triethylamine). An 82 mg portion of (S)-2 provided 100 mg (92%) of (S)-3 as a colorless oil. The $^1$H NMR spectrum of (S)-3 was the same as for (R)-3. Anal. (C$_{16}$H$_{27}$FN$_4$O$_4$).

Example 4

This example illustrates synthesis of (R)-2-amino-3-[1-(2-fluoroethyl)-1H-[1,2,3]triazol-4-yl]propanoic acid hydrochloride salt (compound (R)-4) and (S)-2-amino-3-[1-(2-fluoroethyl)-1H-[1,2,3]triazol-4-yl]propanoic acid hydrochloride salt (compound (S)-4) (FIG. 1).

To synthesize compound (S)-4, a 45 mg portion of (R)-3 (0.13 mmol) was dissolved in 2 mL of methanol and 2 mL of 1 M aqueous hydrochloric acid in a screw-top vial. The reaction mix was heat 60° C. for three hours and then concentrated under reduced pressure. The residue was washed with 3×3 mL of diethyl ether. The resulting oil was dissolved in a small amount of ethanol (~0.5 mL), and the solid product was precipitated by adding 10 mL of diethyl ether. The supernatant was removed to provide (R)-4 as a faintly yellow solid (23 mg, 74%). The $^1$H NMR spectra (D$_6$-DMSO) of the product was: 0.96 (1H, t, J=6.9), 3.14-3.16 (2H, m), 4.10-4.18 (1H, broad m), 4.54-4.58 (1H, m), 4.62-4.67 (2H, m), 4.78-4.81 (1H, m), 8.53 (3H, broad s). Anal. (C$_7$H$_{12}$ClFN$_4$O$_2$).

To synthesize compound (S)-4, a 30 mg portion of (S)-3 (0.083 mmol) was dissolved in 3 mL of 1M aqueous hydrochloric acid in a screw-top vial and heated at 60° C. for 3 hours. The solvent was removed under reduced pressure, and the residue was triturated with 0.5 mL of ethanol to provide a white solid. Residual ethanol was removed under reduced pressure, and the resulting white solid was washed with 3×3 mL of diethyl ether to provide (S)-4 (17 mg, 86%) as a white solid. The $^1$H NMR spectrum of (S)-4 was the same as for (R)-4. m.p. Anal. (C$_7$H$_{12}$ClFN$_4$O$_2$).

The enantiomeric purity of (R)-4 and (S)-4 was evaluated by chiral HPLC analysis with a 4.6×150 mm Chirex 3126 (D)-Penicillamine column (Phenomenex, Torrance Calif., USA). The mobile phase consisted of 85:15 aqueous 3 mM copper (II) sulfate pentahydrate:acetonitrile with a flow rate of 1.5 mL/min and UV detection (l=254 nm). The same HPLC system was used for analysis of the fluorine-18 labeled products.

The syntheses illustrated in FIG. 1 can be summarized as follows:

a) 1.5 eq (Boc)$_2$O, 9:1 CH$_3$OH, Et$_3$N;
b) Cl$_3$CC(=NH)OtBu, CH$_2$Cl$_2$;
c) FCH$_2$CH$_2$N$_3$, CuI, DMF/THF;
d) conc. aqueous HCl, EthOH, 60° C.,
wherein Boc is tert-butoxy carbonyl and tBu is terry-butyl.

Example 5

Figure 2:
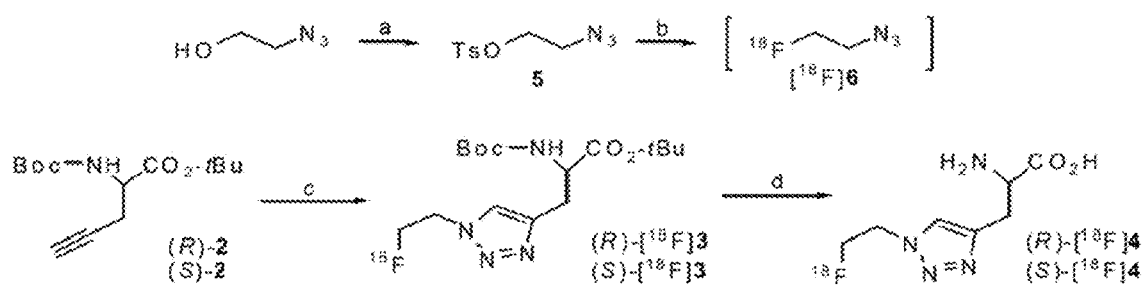
FIG. 2 illustrates the radiolabeling of (R)-[$^{18}$F]4 and (S)-[$^{18}$F]4.

This example illustrates synthesis of 2-azido-1-(4-methylbenzenesulfonate)-ethanol (compound 5) (FIG. 2).

To synthesize compound 5, a reaction was performed based on the procedure reported in Demko et al., Org. Len. 3: 4091-4094, 2001, with minor modifications.

A 4.0 g portion of 2-bromo-1-ethanol (32.0 mmol) was added to 10 mL of water followed by 2.5 g of sodium azide (38.5 mmol), and the reaction mix was heated at reflux overnight. After cooling, the reaction mix was extracted with 3×10 mL of dichloromethane, and the combined organic phases were dried over anhydrous magnesium sulfate and filtered. A 1.5 equivalent of p-toluenesulfonyl chloride (9.15 g) and 2.0 equivalent portion of triethylamine (8.9 mL) were added to the filtrate, and the reaction mix was stirred at room temperature overnight. The reaction mix was then washed with 2×20 mL of water followed by usual work up. Purification by silica gel flash chromatography (2:8 ethyl acetate:hexane) provided compound 5 as a faintly yellow oil (5.1 g, 66%) at room temperature which formed a solid at −30° C. The $^1$H NMR spectra (300 MHz, CDCl$_3$) of the product was: 2.47 (3H, s) 3.47-3.51 (2H, m), 4.15-4.18 (2H, m), 7.36-7.39 (2H, m), 7.80-7.84 (2H, m).

Example 6

Radiosynthesis

This example illustrates the radiosynthesis of (R)-2-amino-3-[1-(2-fluoroethyl)-1H-[1,2,3]triazol-4-yl]propanoic acid hydrochloride salt-[$^{18}$F] (compound (R)-[$^{18}$F]4) and (S)-2-amino-3-[1-(2-fluoroethyl)-1H-[1,2,3]triazol-4-yl]propanoic acid hydrochloride salt-[$^{18}$F] (compound (S)-[$^{18}$F]4), as shown in FIG. 2. The identical procedure was used for the radiosynthesis of (R)-[$^{18}$F]4 and (S)-[$^{18}$F]4 starting from the enantiomerically pure alkynes (R)-2 and (S)-2, respectively. The following illustrates the procedure for the radiosynthesis of (R)-[$^{18}$F]4.

The [$^{18}$F]fluoride used for radiosyntheses was produced from H$_2$[$^{18}$O]O using the $^{18}$O(p,α)$^{18}$F reaction in a CTI RDS 111 cyclotron at the Washington University in St Louis Cyclotron Facility. Typical radiosyntheses were performed with 50 to 150 mCi of potassium [$^{18}$F]fluoride eluted from a trap and release cartridge in 200 to 1000 μL of a 0.1 M aqueous solution of potassium carbonate. A 5 mg portion of K$_{222}$ Kryptofix in 1 mL of anhydrous acetonitrile and a 1 mg portion of potassium carbonate in 0.1 mL of water were added to the aqueous K[$^{18}$F]F in a borosilicate vial with a screw top cap. The solution was then azeotropically dried with acetonitrile.

The 2-[$^{18}$F]fluoroethyl azide (compound [$^{18}$F]6) was prepared by adding 1.5 mg portion of the tosylate precursor compound 5 (6.2 μmol) in 0.2 mL of anhydrous acetonitrile to the dried [$^{18}$F]fluoride. The reaction vial was sealed and heated to 85° C. for 15 min. The reaction vial was then allowed to cool at ambient temperature for 2 to 3 min prior to use in the next step. The incorporation of [$^{18}$F]fluoride could be estimated at this point by spotting the crude reaction mix on a silica TLC plate (6:4 ethyl acetate:hexane, Rf=0.6).

The cycloaddition reaction was performed by adding a mixture of 50 μL of 1.5 M aqueous sodium L-ascorbate and 50 μL of 0.45 M of aqueous copper (II) sulfate pentahydrate in a syringe prepared immediately before use to the dried [$^{18}$F]fluoride followed by 5 mg of the alkyne precursor (R)-2 (19 μmol) in 0.1 mL of N,N-dimethylformamide. The reaction vial was sealed, and the reaction was allowed to proceed at room temperature for 15 min with intermittent gentle shaking. The reaction mix was diluted with 2 mL of acetonitrile and then passed in series through a cotton plug and an Alumina N light SepPak Plus (preconditioned with 10 mL of acetonitrile). Formation of the crude intermediate (R)-2-[N-(tert-butoxycarbonyl)amino]-3-[1-(2-fluoroethyl)-1H-[1,2,3]triazol-4-yl]propanoic acid tert-butyl ester (compound (R)-[$^{18}$F]3) was evaluated by silica TLC (6:4 ethyl acetate:hexane, Rf=0.2). The eluate was concentrated to approximately 1 mL by blowing nitrogen over the surface while heating at 105° C.

Purification of the intermediate (R)-[$^{18}$F]3 was performed by diluting the solution with 2 mL of water and injecting the resulting solution through a 0.45 □m nylon filter onto a Zorbax SB C-18 HPLC column (10×250 mm, 5 μm particle size; Agilent Technologies, Santa Clara Calif., USA). The elution was performed with a mobile phase consisting of 5:6 acetonitrile:0.1 M ammonium acetate, a flow rate of 3 mL/min and radiometric and UV detection (λ=220 nm). The HPLC fractions containing radioactivity eluting at the appropriate retention time (17 min) were collected separately and combined. Solid phase extraction (SPE) of the purified intermediate was performed by diluting the combined fractions with water (15:1 water:eluate volume) and passing the solution through a classic C-18 SepPak preconditioned with 10 mL of acetonitrile and then 10 mL of water. The intermediate (R)-[$^{18}$F]3 was eluted from the C-18 SepPak with 0.5 mL portions of acetonitrile with the vast majority of the product typically eluting in the $2^{nd}$ and $3^{rd}$ fractions. The acetonitrile solution containing the radiolabeled intermediate was concentrated by blowing nitrogen over the surface while heating at 105° C. in a borosilicate glass vial. A 0.5 mL portion of a 1 M aqueous hydrochloric acid was added to the residue, the vial was sealed with a screw top cap, and the reaction mix was heated with a 60 W microwave for 30 sec.

Two methods were used for formulating the final product (R)-[$^{18}$F]4 for biological studies. The first method, for rodent biodistribution and MicroPET studies, the aqueous hydrochloric acid solution was neutralized by adding an equal volume of 100 mg/mL of sodium bicarbonate in sterile 0.9% saline. After addition of the sodium bicarbonate, the desired concentration of (R)-[$^{18}$F]4 was achieved through dilution with 0.9% saline. The final doses were passed through a 0.22 μm nylon filter prior to use in rodent studies. The second method, for cell uptake studies, the aqueous hydrochloric acid solution containing the final product was added to and rapidly eluted with water through a 8×60 mm column of AG 11A8 ion retardation resin preconditioned with 50 mL of water. Fractions containing radioactivity were collected and diluted to the desired concentration with water for use in cell uptake studies.

The radiochemical purity, enantiomeric purity, and specific activity of the final product (R)-[$^{18}$F]4 were evaluated after dose formulation. TLC analysis was performed with silica plates developed with 1:1 methanol:water. HPLC analysis was performed with 4.6×150 mm Chirex 3126 (D)-penicillamine chiral column eluted with a mobile phase consisting of 85:15 aqueous 3 mM copper (II) sulfate pentahydrate:acetonitrile, a flow rate of 1.5 mL/min and radiometric and UV detection (λ=254 nm). The identity of the product was confirmed by HPLC coinjection of non-radioactive (R)-4 and (S)-4. The specific activity of the product was determined by comparing the UV absorbance associated with the radiolabeled product to a standard curve obtained by injecting varying amounts of non-radioactive (R)-4 or (S)-4

The procedure contained herein can be used for the synthesis of (S)-[$^{18}$F]4 starting from the pure alkyne (S)-2.

The total synthesis time was approximately 2.5 hours with (R) and (S)-[$^{18}$F]4 obtained in decay corrected yields of 57±6% (n=3) and 51±8% (n=5), respectively. The radiochemical purity was greater than 99% after acidic deprotection and dose formulation with sodium bicarbonate for both enantiomers. Some decomposition of the final product was observed after passage of the product through the ion-retardation resin, particularly if the final product was left on the column for a prolonged period of time. The radiochemical purity of the final product after the ion-retardation column was greater than 94%. The estimated enantiomeric purity of both the (R)- and the (S)-[$^{18}$F]4 final products was greater than 98% enantiomer excess (e.e.) with the undesired enantiomer undetectable by chiral HPLC. The estimated specific activities of the final products used in biological studies were at least 1 Ci/μmole for the (S)-enantiomer and >0.3 Ci/μmole for the (R)-enantiomer. These values represent lower limits of specific activities as the sensitivity of UV detection was limited for the low concentrations of non-radioactive (R)- and (S)-4 in the final product, particularly for the (R)-enantiomer with its broader HPLC peak.

The syntheses illustrated in FIG. 2 can be summarized as follows:
  a) 1.5 eq TsCl, Et$_3$N, CH$_2$Cl$_2$;
  b) K[$^{18}$F]F, K$_{222}$, K$_2$CO$_3$;
  C) [$^{18}$F]6, Cu(SO$_4$), sodium L-ascorbate;
  d) conc. aqueous HCl, microwave heating, wherein Ts is CH$_3$C$_6$H$_4$SO$_2$ Example 7

Cell Uptake Assays

The 9L gliosarcoma tumor is an established model for human glioblastoma (brain tumor). Cell uptake assays were performed with 9L gliosarcoma cells using both (R)-[$^{18}$F]4 and (S)-[$^{18}$F]4. 9L gliosarcoma cells were cultured with Earle's minimal essential medium (MEM) augmented with 10% newborn calf serum, 1% 200 mM L-glutamine, 1% MEM vitamin solution and 1% 10 mM non-essential amino acids (NEAA). The cells were passaged every two to three days prior to use with no more than a total of 20 passages. Two to three days before the uptake assays, suspension of 2.5 or 5.0×10$^4$ cells in culture media were aliquoted into Costar 24 well plates to achieve log growth phase with approximately 70% confluency at the time of the uptake assay (approximately 10$^5$ cells per well).

Cell uptake assays were performed using the cluster tray method reported in Gazzola et al., Anal. Biochem. 115: 368-374, 1981. Two buffers were used for the assays, a phosphate buffered saline solution and a sodium-free phosphate buffered choline chloride solution. The sodium buffer consisted of 105 mM sodium chloride, 3.8 mm potassium chloride, 1.2 mM potassium bicarbonate, 25 mm of sodium phosphate dibasic, 0.5 mM calcium chloride dehydrate, 1.2 mM magnesium sulfate and 5.6 mM of D-glucose. The choline buffer was the same as the sodium buffer except choline chloride was substituted for sodium chloride and choline phosphate dibasic was substituted for sodium phosphate dibasic. A 250 mM solution of choline phosphate dibasic was prepared by boiling 95.6 mL of 75% of choline bicarbonate (0.500 mol) and 16.9 mL of 85% aqueous phosphoric acid (0.247 mol) in 750 mL of water for 60 min. The solution was brought to a total volume of 1 liter with water and brought to pH 7.4 with concentrated aqueous hydrochloric acid. The pH of the sodium and choline buffer solutions was adjusted to 7.4 with concentrated aqueous hydrochloric acid prior to use.

A variety of inhibitor conditions were used to determine which amino acid transport system or systems were responsible for cellular uptake of (R)- and (S)-[$^{18}$F]-4. The N-methylated amino acid, methylaminoisobutyric acid (MeAIB), is a selective system A substrate and has been used extensively as a competitive inhibitor of system A transport (Shotwell, M. A., et al. Biochem. Biophys. Acta. 737: 267-284, 1983; Christensen, H. N., et al., J. Biol. Chem. 240: 3609-3616, 1965) The bulky neutral amino acid, 2-aminobicyclo-(2,2,1)-heptane-2-carboxylic acid (BCH), has been extensively used as a competitive inhibitor of system L transport, and under sodium-free conditions BCH is a selective system L inhibitor (Palacin, M., et al., Physiol. Rev. 78: 969-1054, 1998. In the presence of sodium, BCH is also an inhibitor of system $B^{0,+}$ which is a sodium-dependent amino acid transporter that typically is a minor transport systems in most tissues. A mixture of L-alanine (L-Ala), L-serine (L-Ser) and L-cysteine (L-Cys), (ASC), was used as a non-specific inhibitor condition, and this combination of amino acids is expected to inhibit a broad range of amino acid transport systems including system ASC. Because of the results of initial cell uptake assays described below and the structural relationship of the 1H-1,2,3-triazole group to the imidazole side chain of L-histidine (L-His), additional uptake assays using L-His as well as the basic side chain amino acids L-arginine (L-Arg) and L-lysine (L-Lys) individually and together (RKH) as competitive inhibitors were performed.

The following inhibitors were added to the appropriate sodium or choline buffer: N-methyl aminoisobutyric acid (MeAIB, 10 mM), a mixture of L-alanine/L-serine/L-cysteine (ASC, 3.3 mM of each amino acid), (R,S)-(endo,exo)-2-aminobicyclo(2,2,1)-heptane-2-carboxylic acid (BCH, 10 mM), L-arginine (Arg, 10 mM), L-lysine (Lys, 10 mM), L-histidine (His, 10 mM) and a mixture of Arg/Lys/H is (RKH, 3.3 mM of each amino acid). For control conditions, 10 mM of sucrose was added to maintain consistent osmolality relative to the inhibitor conditions. The pH of each solution of inhibitor in buffer was adjusted as necessary to 7.40 with 3 M aqueous hydrochloric acid prior to use in cell uptake assays. The assay buffers with inhibitors were then formulated with radiotracer by adding 20 µL/mL of the radiolabeled amino acid (R)-[$^{18}$F]4 or (S)-[$^{18}$F]4 at a concentration of 1-2 mCi/mL to each control and inhibitor condition. From each assay condition with radiotracer, a 100 µL sample was taken as a standard to determine the total amount of radioactivity added to each well.

Each 24 well plate was used for 6 assay conditions with each conditions performed in quadruplicate. The cell uptake assays were initiated by rinsing the cells with 2×2 mL of the appropriate sodium or choline buffer without inhibitor at 37° C. and then adding 0.4 mL of the appropriate assay buffer at 37° C. with inhibitor and (R)-[$^{18}$F]4 or (S)-[$^{18}$F]4. Uptake was allowed to proceed for 30 sec and then terminated by rinsing the cell wells with 3×2 mL of the appropriate ice-cold buffer. Residual fluid was removed by pipet, and 200 µL aliquots of aqueous 0.2 M NaOH/0.2% sodium dodecylsulfate lysis buffer were added to each cell well. The plate was then agitated at room temperature for 30 min, and 100 µL of the lysate was taken from each well for counting. Additional 20 µL aliquots were taken in triplicate from each well for protein concentration determination using the Pierce bicinchoninic acid (BCA) protein assay kit (Rockford Ill., USA).

The amounts of radioactivity in each sample from each well and the standard counts for each condition were measured as counts per minute (cpm) using a gamma counter and decay corrected for elapsed time. The cpm values of each well were normalized to the amount of radioactivity added to each well and the protein concentration in the well and expressed as percentage uptake relative to the sodium control condition. The data from each plate was analyzed with a 1-way analysis of variance (ANOVA) with Tukey post-tests using GraphPad Prism software (LaJolla Calif., USA) with p-values less than or equal to 0.05 considered statistically significant.

Figure 3:
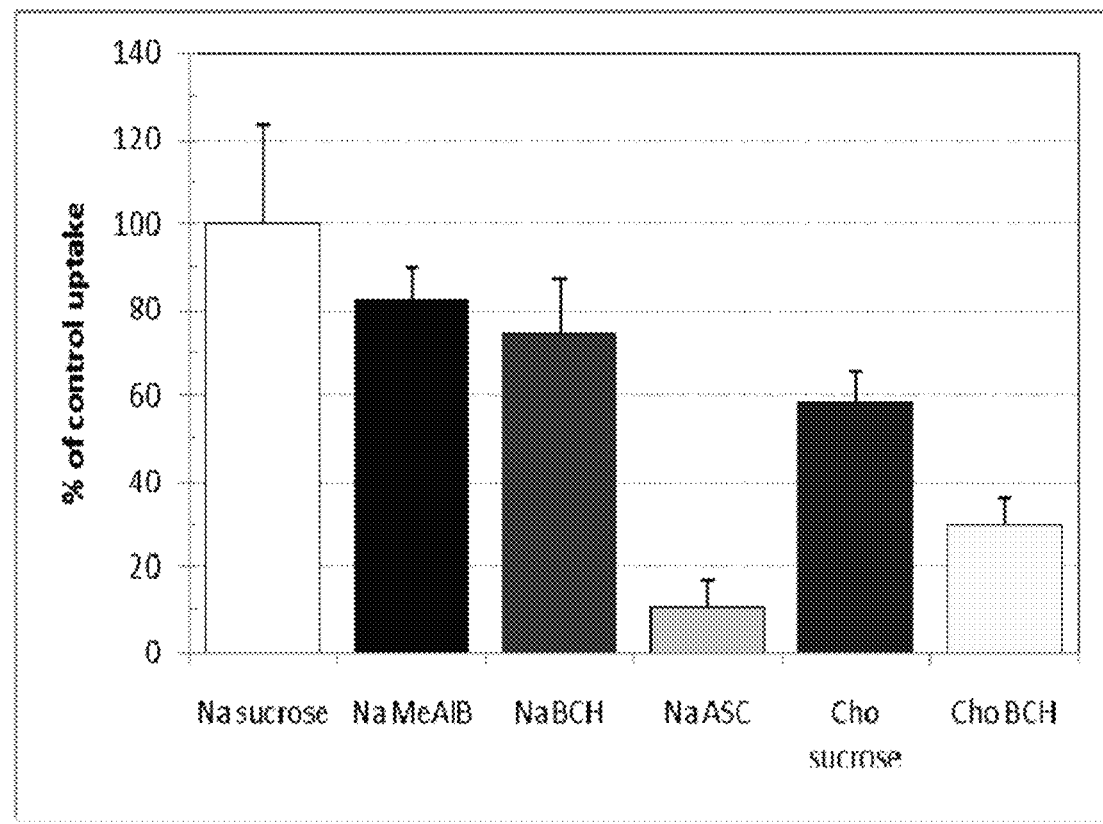
FIG. 3 presents in vitro 9L gliosarcoma cell uptake of (S)-[$^{18}$F]4 with neutral amino acid inhibitors.

Initial cell uptake assays were performed with MeAIB, BCH and ASC inhibitor conditions primarily to evaluate the role of system A and system L transport in the uptake of both enantiomers of [$^{18}$F]4 by 9L gliosarcoma cells. In the case of (S)-[$^{18}$F]4, there was no significant inhibition of uptake by MeAIB, indicating that (S)[$^{18}$F]4 is not a substrate for system A transport under these assay conditions. In contrast, the ASC condition inhibited 89% of uptake relative to the sodium control (p<0.001), indicating that almost all of the cell uptake of (S)-[$^{18}$F]4 was mediated by amino acid transport. Additionally, substituting choline for sodium led to a 42% inhibition of uptake (sodium control vs. choline control, p<0.001), consistent with a sodium dependent component of transport of (S)-[$^{18}$F]4. In the sodium free conditions, the addition of BCH led to an approximately 50% reduction of the total uptake relative to the choline control (p<0.05). The inhibition of uptake by BCH under sodium free conditions indicates that (S)-[$^{18}$F]4 is a substrate for system L transport, accounting for approximately 28% of total uptake. A similar magnitude of inhibition by BCH was observed in the presence of sodium (sodium control vs sodium BCH) with a 26% inhibition versus control (p<0.01). These data are depicted in FIG. 3. The following percent uptake values relative to control were measured: Na MeAIB=82±7%, Na BCH=74±13%, Na ASC=11±7%, Cho sucrose=58±7%, Cho BCH=30±6%. 1-way ANOVA results: for Na sucrose vs Na ASC, Na sucrose vs Cho BCH, Na MeAIB vs Na ASC, Na MeAIB vs Cho BCH, Na BCH vs Na ASC, and Na ASC vs Cho sucrose p<0.001; for Na sucrose vs Cho sucrose and Na BCH vs Cho BCH p<0.01; for Cho sucrose vs Cho BCH p<0.05. In FIG. 3, Na=sodium buffer, Cho=choline buffer, MeAIB=N-methyl α-aminoisobutyric acid (system A inhibitor), BCH=2-aminobicyclo(2,2,1)-heptane-2-carboxylic acid, ASC=L-Ala, L-Ser, L-Cys mixture, RKH=L-Arg, L-Lys, L-His mixture. The Na sucrose and Cho sucrose conditions represent controls for the sodium containing and sodium free conditions, respectively.

Figure 4:
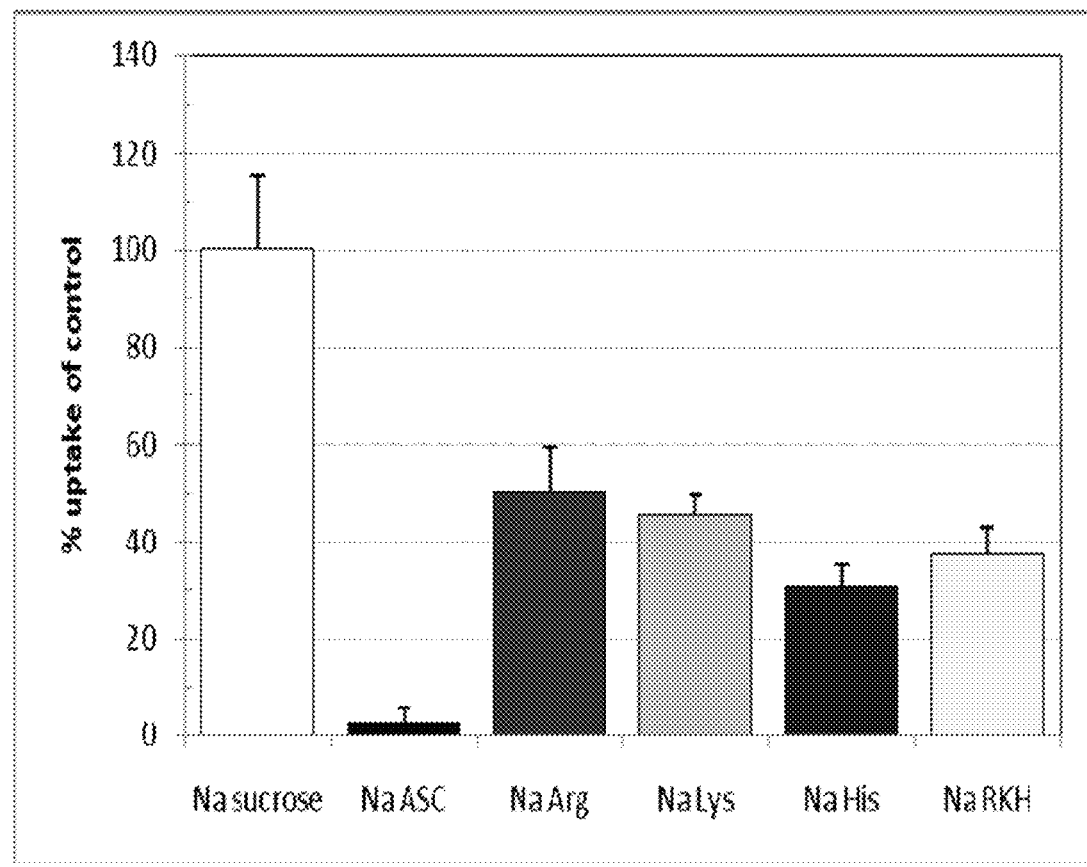
FIG. 4 presents in vitro 9L gliosarcoma cell uptake of (S)-[$^{18}$F]4 with basic side chain amino acid inhibitors.

The initial assays with (S)-[$^{18}$F]4 demonstrated that this compound enters cells primarily via sodium-dependent and sodium-independent amino acid transport with approximately 30% of uptake mediated by system L. Because of the similarity of the 1-1,2,3-triazole group with the imidazole substituent of L-His, a second assay was performed using amino acids with basic side chains including L-His, L-Arg and L-Lys. Each of these amino acids inhibited uptake of (S)-[$^{18}$F]4 relative to control, with the magnitude of inhibition ranging from 50% with L-Arg to 69% with L-His (p<0.001 for each condition). The inhibitory effect of L-His was greater than that of L-Ariz. (p<0.05) but was not significantly different than with L-Lys. These data are compatible with (S)-[$^{18}$F]4 entering 9L gliosarcoma cells via cationic amino acid transport systems and are depicted in FIG. 4. The following percent uptake values relative to control were measured: Na ASC=2.4±3.5%, Na Arg=50±9%, Na Lys=46±4%, Na His=31±5%, Na RKH=37±6%. 1-way ANOVA results: Na sucrose vs Na ASC, Na sucrose vs Na Arg, Na sucrose vs Na Lys, Na sucrose vs Na His, Na sucrose vs RKH, Na ASC vs Na Arg, Na ASC vs Na Lys, and Na ASC vs Na RKH p<0.001; for Na ASC vs Na His p<0.01.

Figure 5:
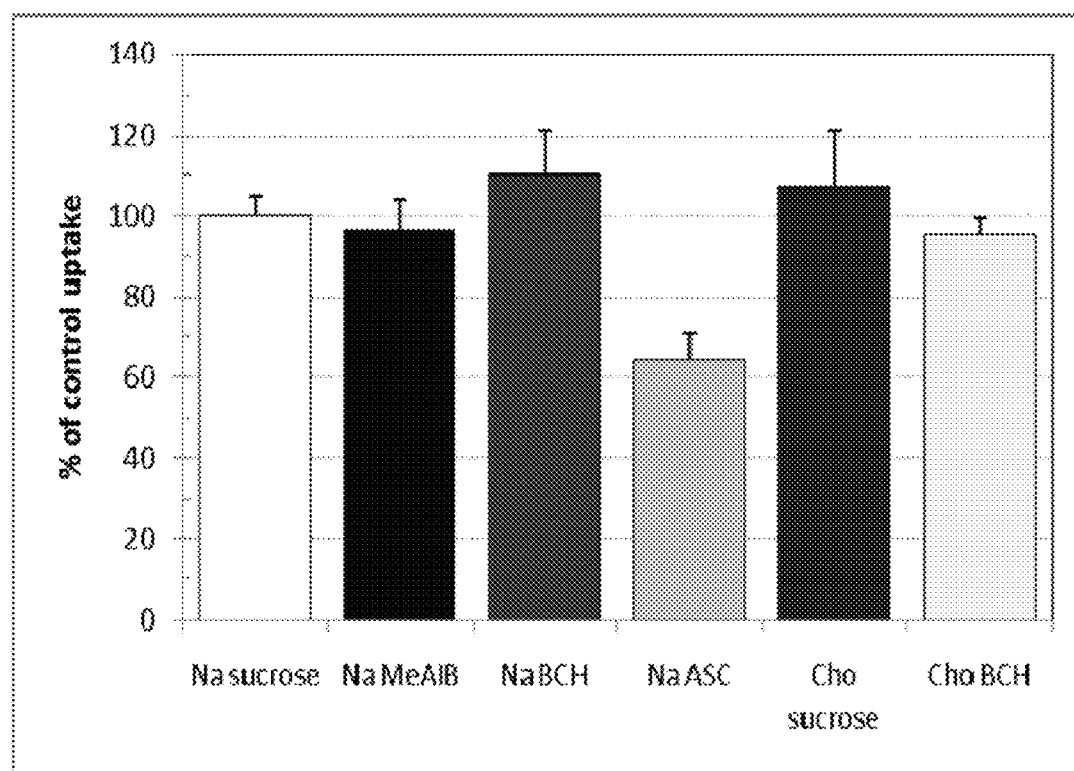
FIG. 5 presents in vitro 9L gliosarcoma cell uptake of (R)-[$^{18}$F]4 with neutral amino acid inhibitors.
Figure 6:
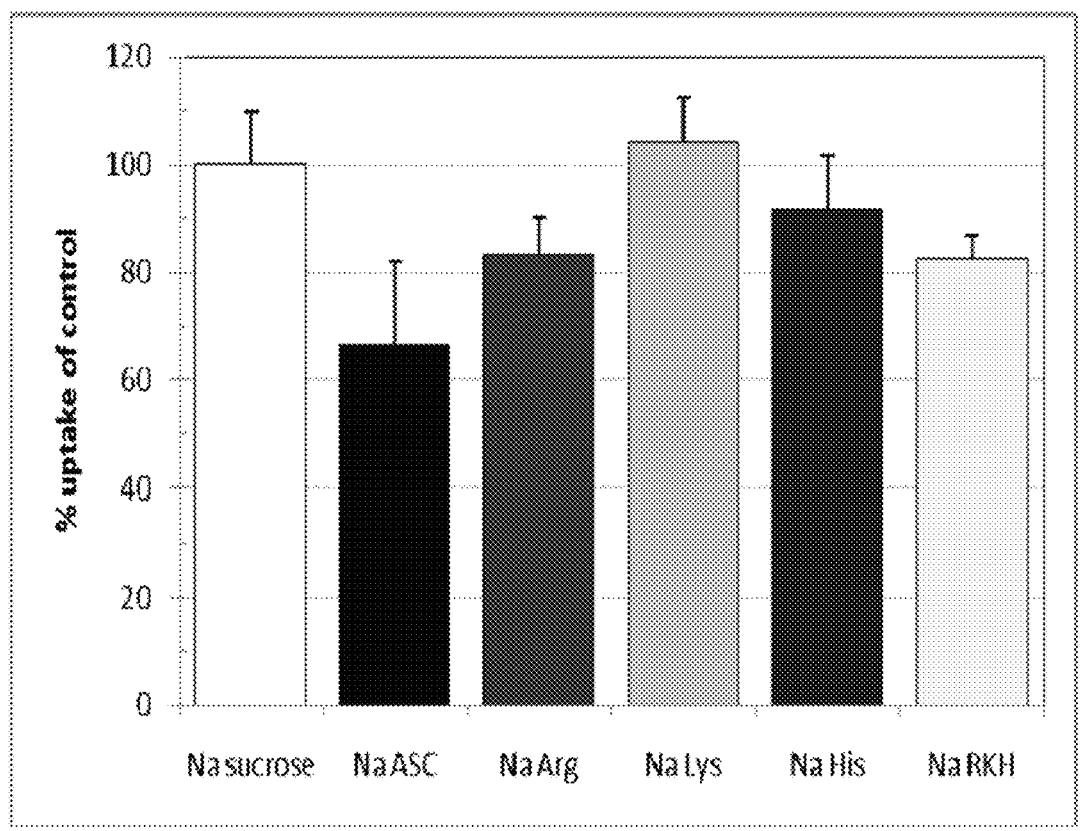
FIG. 6 presents in vitro 9L gliosarcoma cell uptake of (R)-[$^{18}$F]4 with basic side chain amino acid inhibitors.

In contrast, the same uptake assays performed with (R)-[$^{18}$F]4 did not demonstrate significant uptake mediated by system L or cationic amino acid transport systems. Inhibition of uptake was observed with the non-specific ASC condition (33% with p<0.01 and 36% with p<0.001 in 2 independent assays), but this inhibition did not account for the majority of uptake. These results indicate that the cell uptake of (R)-[$^{18}$F]4 under these assay conditions was mediated by amino acid transport systems not affected by the inhibitors used in these studies or alternatively was not mediated by amino acid transport systems. These results demonstrate that stereochemistry at the □-carbon has a substantial effect on the biologic transport of [$^{18}$F]4. These data are shown in FIG. 5. The following percent uptake values relative to control were measured: Na MeAIB=97±7%, Na BCH=110±11%, Na ASC=64±6%, Cho sucrose=107±14%, Cho BCH=95±4%. 1-way ANOVA results: for Na sucrose vs Na ASC, Na MeAIB vs ASC, Na BCH vs Na ASC, and Na ASC vs Cho sucrose p<0.001; for Na ASC vs Cho BCH p<0.01. These data are also shown in FIG. 6. The following percent uptake values relative to control were measured: Na ASC=67±15%, Na Arg=83±7%, Na Lys=104±8%, Na His=91±10%, Na RKH=82±4%. 1-way ANOVA results: Na sucrose vs Na ASC and Na ASC vs Na Lys p<0.01; for Na ASC vs Na His p<0.05.

In summary, the in vitro uptake of (S)-[$^{18}$F]4 by 9L gliosarcoma cells a combination of cationic amino acid transport and to a lesser extent system L transport appears to mediate the majority of (S)-[$^{18}$F]4 uptake by 9L cells. The entry of cationic amino acids into cells can be mediated by multiple types of amino acid transporters. The cationic amino acid transporter (CAT) family has four known members (CAT-1, CAT-2A, CAT-2B, CAT-3), and transport by the CAT family is sodium-independent. Other sodium-independent transport systems that recognize cationic amino acid transporters include system y$^{30}$ L and system B$^{0,+}$ (Furesz et al. Am J Physiol Cell Physiol. 1991; 261: C246-C252). Transport of (S)-[$^{18}$F]4 by one or more of these transport systems is compatible with the sodium-independent transport observed in the uptake assays. Cationic amino acids can also be transported by system B$^{0,+}$ in a sodium-dependent fashion which may account for the some or all of the sodium-dependent transport of (S)-[$^{18}$F]4 (Closs, E. I., et al., J. Membr. Biol. 213: 67-77, 2006; Closs, E. I., Curr. Opin. Nephrol. Hypertens. 11:99-107, 2002).

Example 8

Biodistribution Studies With (R—[$^{18}$F]4 and (S)-[$^{18}$F]4 in Rats with Subcutaneous 9L Tumors This example describes the results of in vivo studies on the biodistribution of both (R)-[$^{18}$F]4 and (S)-[$^{18}$F]4. Biodistribution studies were performed with both enantiomers, (R)-[$^{18}$F]4 and (S)-[$^{18}$F]4, using Fischer 344 rats (Charles River Laboratories, Wilmington Mass., USA) implanted with subcutaneous 9L gliosarcoma tumors. The tumors were implanted by subcutaneous injection of a suspension of approximately 1×10$^6$9L gliosarcoma cells into the flanks of the rats. The tumors were allowed to grow for 3 weeks prior to the study. The rats were allowed food and water ad libitum prior to the biodistribution study. Anesthesia was achieved using a mixture of 1% isoflurane in oxygen, and the radiolabeled amino acid (R)-[$^{18}$F]4 or (S)-[$^{18}$F]4 was injected intravenously through a tail vein. The animals were euthanized in groups of four for each enantiomer at 5, 30 or 60 minutes after injection. The organs and tissues of interest and the tumors were dissected and weighed, and the amounts of activity were measured and decay corrected to the time of injection with a gamma counter. Standards for the doses were also measured with a gamma counter, and the data were normalized as the percent of total dose per gram of tissue (% ID/g) for each sample. The data were analyzed using GraphPad Prism software with 1-way ANOVAs for each enantiomer at each time point with Bonferroni post-tests. The tumor and brain uptake of radioactivity was directly compared for both enantiomers at each time point with a 2-way ANOVA with Bonferroni post-test. p-values less than or equal to 0.05 were considered statistically significant.

The biodistribution results obtained with (R)- and (S)-[$^{18}$F]4 are presented in Tables 1 and 2.

TABLE 1

Biodistribution of (S)-[$^{18}$F]4 in Fischer rats with subcutaneous 9L gliosarcoma tumors (data expressed as % ID/g ± standard deviation except for the thyroid which is expressed as percent of total dose per organ, n = 3 or 4 for each value)

|  | 5 min | 30 min | 60 min |
| --- | --- | --- | --- |
| blood | 0.98 ± 0.152 | 0.47 ± 0.101 | 0.23 ± 0.015 |
| bone | 0.47 ± 0.065 | 0.36 ± 0.068 | 0.23 ± 0.011 |
| brain | 0.08 ± 0.011 | 0.06 ± 0.008 | 0.05 ± 0.001 |
| fat | 0.09 ± 0.020 | 0.05 ± 0.010 | 0.04 ± 0.007 |
| heart | 0.43 ± 0.048 | 0.38 ± 0.066 | 0.30 ± 0.011 |
| kidney | 11.02 ± 1.224 | 11.41 ± 1.939 | 4.79 ± 0.378 |
| large intestine | 0.14 ± 0.012 | 0.15 ± 0.028 | 0.10 ± 0.012 |
| liver | 0.34 ± 0.035 | 0.43 ± 0.091 | 0.32 ± 0.021 |
| lung | 0.87 ± 0.117 | 0.83 ± 0.179 | 0.56 ± 0.085 |
| muscle | 0.18 ± 0.030 | 0.18 ± 0.037 | 0.16 ± 0.006 |
| pancreas | 2.75 ± 0.634 | 2.20 ± 0.747 | 1.12 ± 0.151 |
| salivary gland | 0.74 ± 0.043 | 0.66 ± 0.139 | 0.36 ± 0.037 |
| small intestine | 0.69 ± 0.076 | 0.54 ± 0.073 | 0.31 ± 0.024 |
| spleen | 0.72 ± 0.054 | 0.75 ± 0.123 | 0.47 ± 0.035 |
| testes | 0.21 ± 0.013 | 0.17 ± 0.033 | 0.11 ± 0.006 |
| thyroid | 0.71 ± 0.117 | 0.44 ± 0.102 | 0.30 ± 0.024 |
| tumor | 0.47 ± 0.069 | 0.83 ± 0.142 | 0.72 ± 0.098 |
| tumor:brain ratio | 5.9 | 14.6 | 15.2 |

TABLE 2

Biodistribution of (R)-[$^{18}$F]4 in Fischer rats with subcutaneous 9L gliosarcoma tumors (data expressed as % ID/g ± standard deviation except for the thyroid which is expressed as percent of total dose per organ, n = 3 or 4 for each value)

|  | 5 min | 30 min | 60 min |
| --- | --- | --- | --- |
| blood | 0.90 ± 0.166 | 0.28 ± 0.037 | 0.14 ± 0.015 |
| bone | 0.32 ± 0.083 | 0.13 ± 0.027 | 0.08 ± 0.007 |
| brain | 0.09 ± 0.015 | 0.04 ± 0.005 | 0.02 ± 0.001 |
| fat | 0.10 ± 0.044 | 0.03 ± 0.012 | 0.02 ± 0.002 |
| heart | 0.42 ± 0.076 | 0.13 ± 0.014 | 0.08 ± 0.006 |
| kidney | 14.01 ± 3.826 | 6.76 ± 0.830 | 2.39 ± 0.138 |
| large intestine | 0.15 ± 0.043 | 0.08 ± 0.060 | 0.05 ± 0.002 |
| liver | 0.54 ± 0.153 | 0.58 ± 0.074 | 0.48 ± 0.023 |
| lung | 0.74 ± 0.143 | 0.54 ± 0.211 | 0.37 ± 0.100 |
| muscle | 0.18 ± 0.049 | 0.08 ± 0.020 | 0.05 ± 0.006 |
| pancreas | 0.53 ± 0.126 | 0.50 ± 0.105 | 0.43 ± 0.063 |
| salivary gland | 0.46 ± 0.083 | 0.20 ± 0.016 | 0.15 ± 0.009 |
| small intestine | 0.32 ± 0.079 | 0.30 ± 0.154 | 0.35 ± 0.015 |
| spleen | 0.33 ± 0.065 | 0.18 ± 0.004 | 0.14 ± 0.002 |
| testes | 0.18 ± 0.042 | 0.08 ± 0.011 | 0.05 ± 0.002 |
| thyroid | 0.64 ± 0.092 | 0.21 ± 0.023 | 0.12 ± 0.010 |
| tumor | 0.27 ± 0.042 | 0.29 ± 0.132 | 0.17 ± 0.009 |
| tumor:brain ratio | 3.2 | 8.8 | 6.9 |

As discussed in detail in this section, (S)-[$^{18}$F]4 demonstrated superior properties for brain tumor imaging compared to (R)-[$^{18}$F]1. At all 3 time points, the magnitude of tumor uptake was higher with (S)-[$^{18}$F]1 than with the (R)-enantiomer (p<0.001 at each time point). In contrast, there was no significant difference between the magnitude of brain uptake at any of the time points with (R)- and (S)-[$^{18}$F]4, with values ranging from 0.02 to 0.09% ID/g. These properties led to maximal tumor to brain ratios of 15.2:1 with (S)-[$^{18}$F]4 at 60 min postinjection and 8.8:1 with (R)-[$^{18}$F]4 at 30 min postinjection. Both compounds demonstrated peak tumor uptake at the 30 min time point with 0.83% ID/g observed for (S)-[$^{18}$F]4 and 0.29% ID/g with (R)-[$^{18}$F]4.

Figure 7:
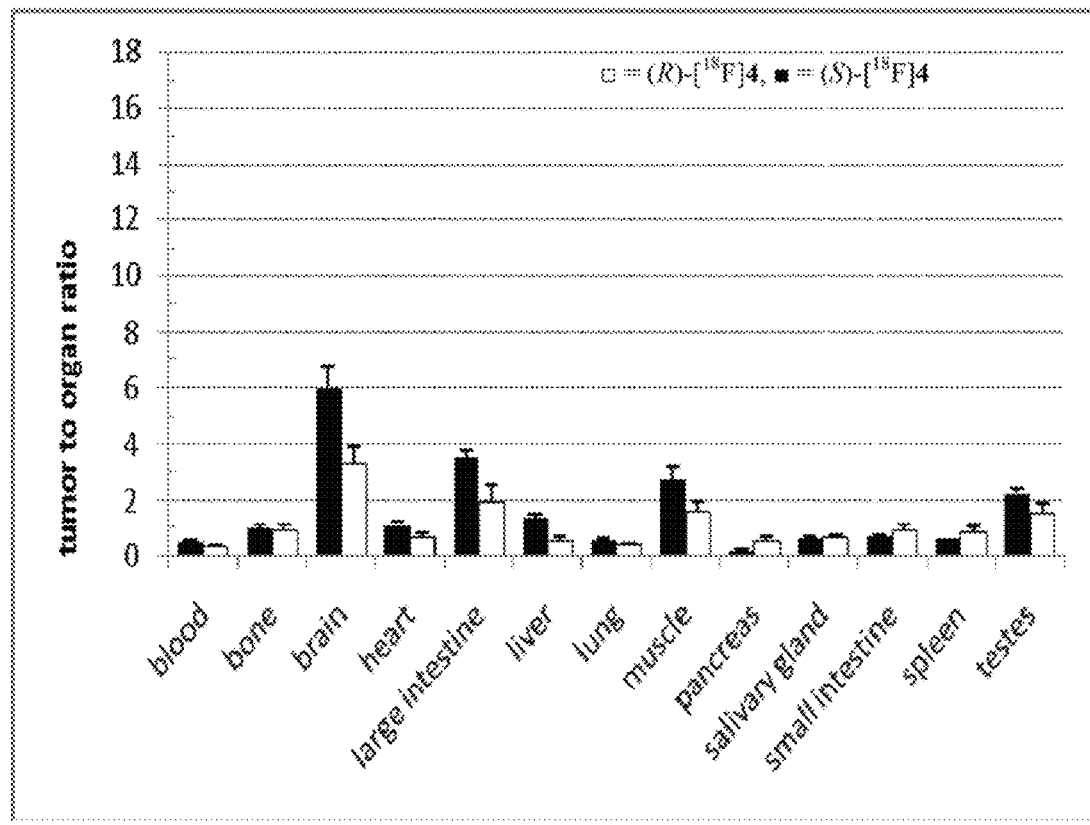
FIG. 7 presents 5 minute tumor to organ ratios with (R)-[$^{18}$F]4 and (S)-[$^{18}$F]4. For FIG. 7-FIG. 9, the graphs depicts the average of the mean tumor uptake (% ID/g) at a given time point divided by the corresponding normal organ/tissue uptake, and the error bars represent standard deviation. n=3 or 4 for each value.
Figure 8:
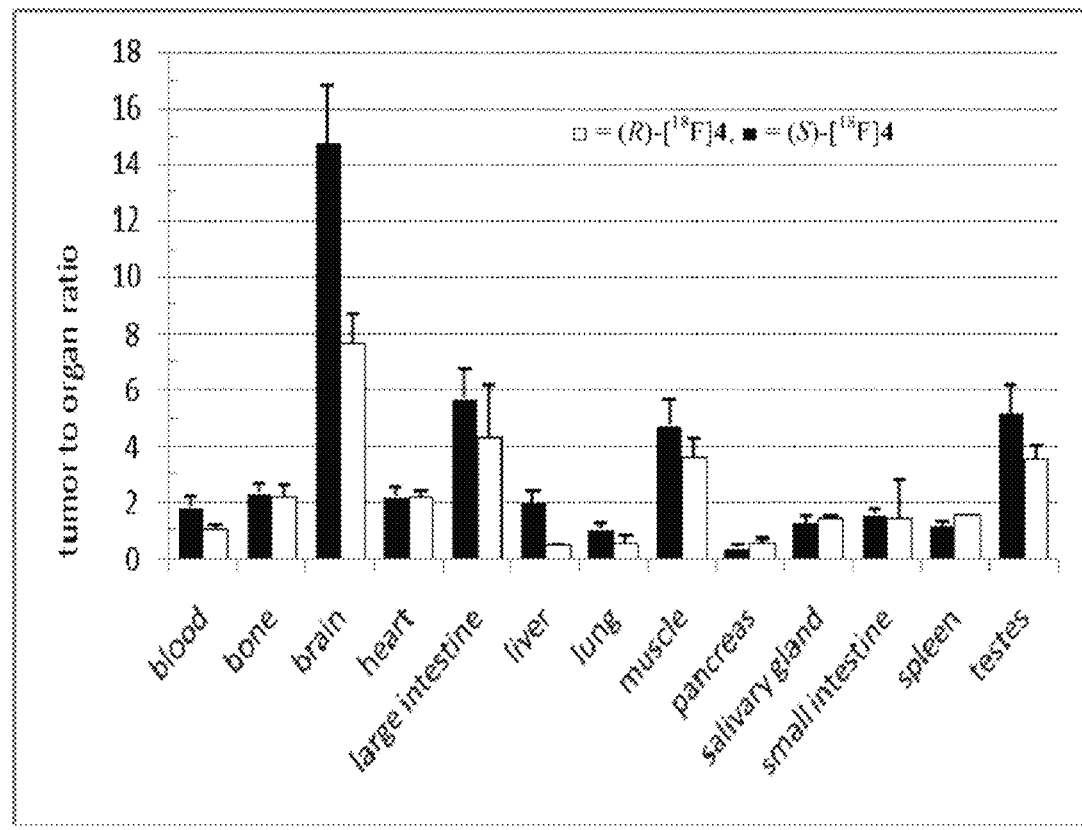
FIG. 8 presents 30 minute tumor to organ ratios with (R)-[$^{18}$F]4 and (S)-[$^{18}$F]4.
Figure 9:
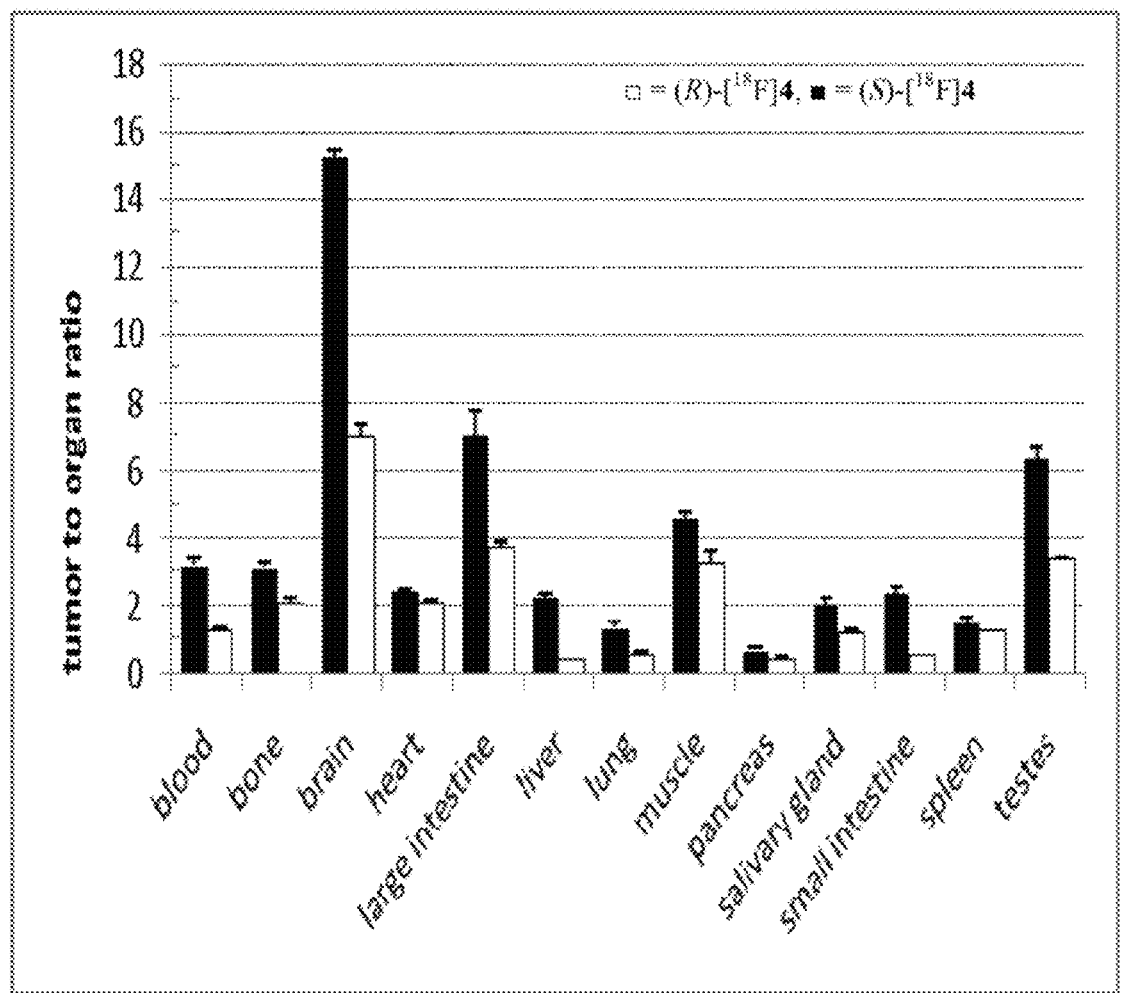
FIG. 9 presents 60 minute tumor to organ ratios with (R)-[$^{18}$F]4 and (S)-[$^{18}$F]4.
Figure 10:
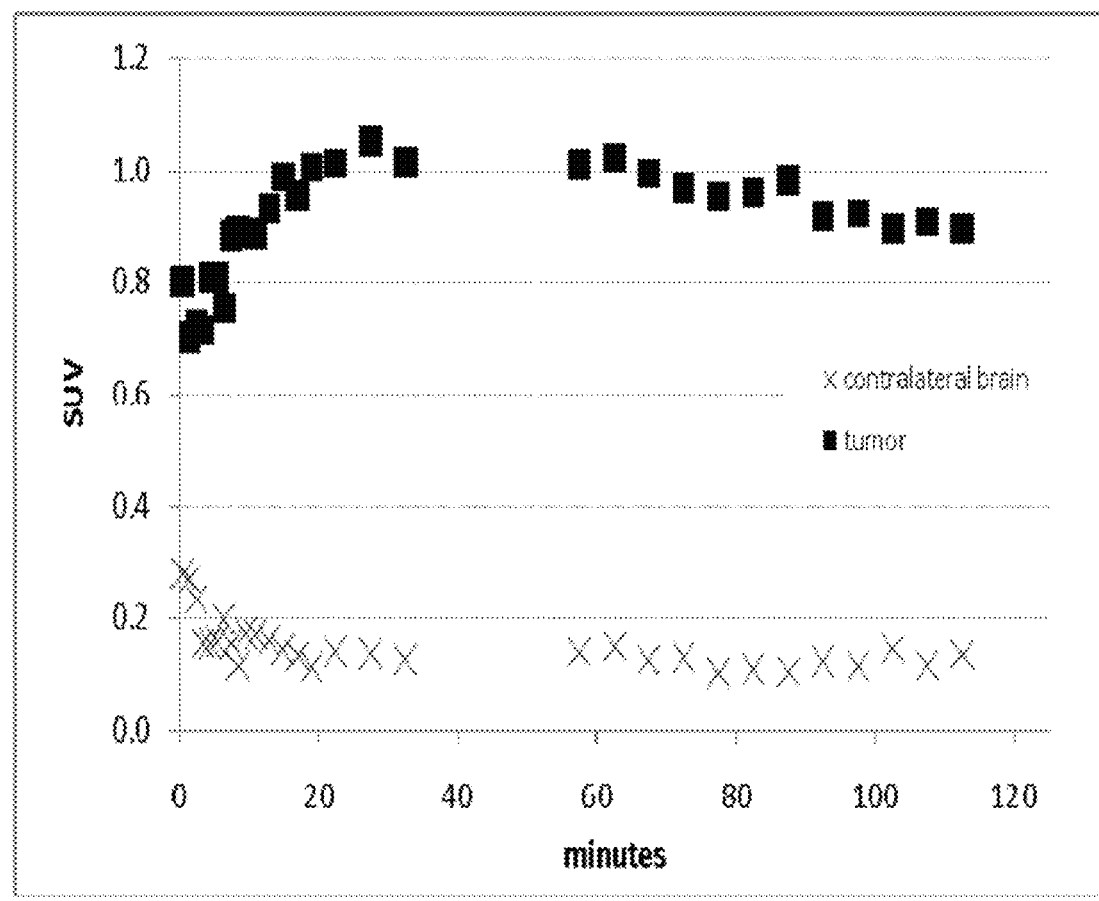
FIG. 10 presents a time-activity curve from MicroPET study performed with (S)-[$^{18}$F]4 in a Fischer rat with an intracranially implanted 9L gliosarcoma tumor. For FIG. 10-FIG. 11, SUV values were calculated as ((nCi/cc)×weight in grams)/(injected dose in nCi).
Figure 11:
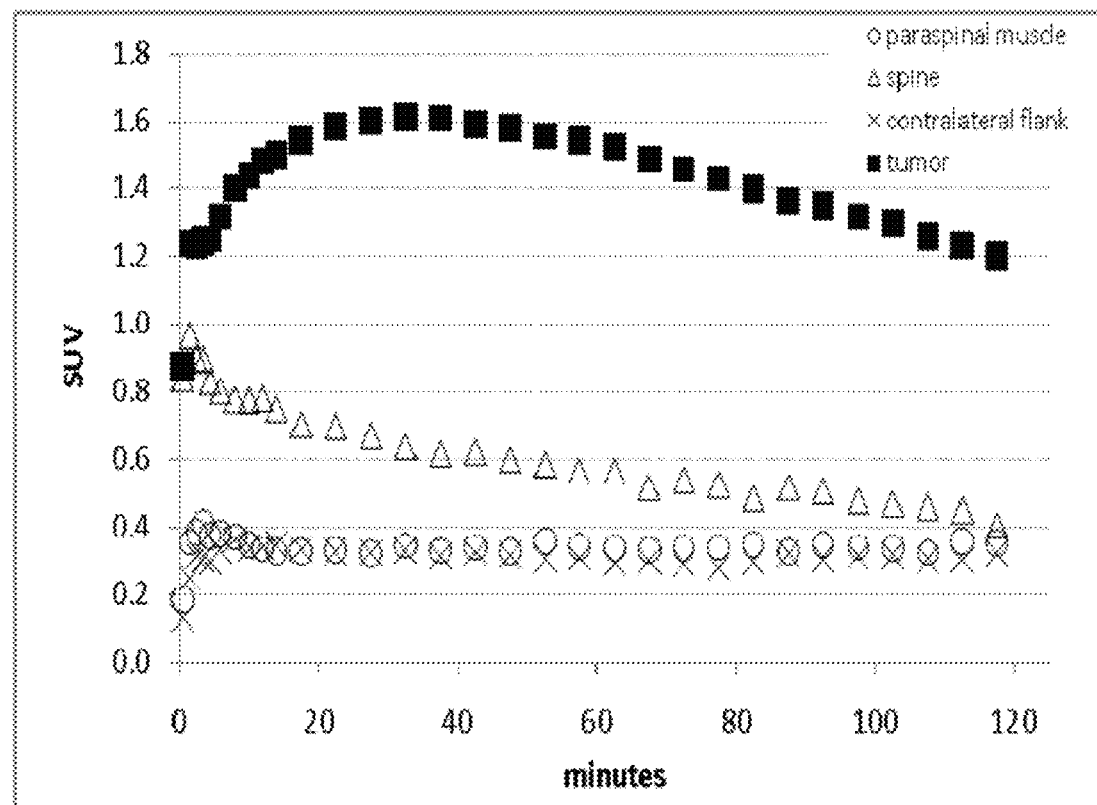
FIG. 11 presents a time-activity curve from MicroPET study performed with (S)-[$^{18}$F]4 in a Fischer rat with a subcutaneously implanted 9L gliosarcoma tumor.
Figure 12:
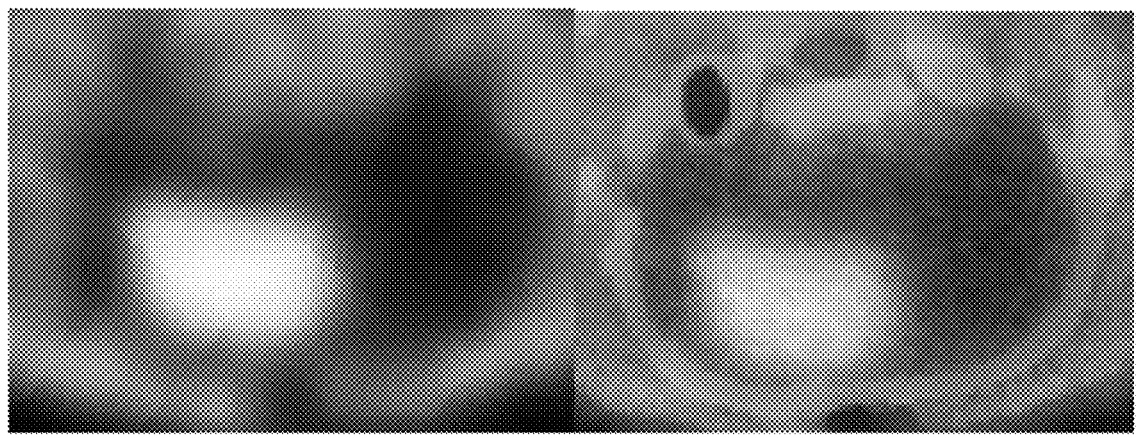
FIG. 12 shows PET and fused PET/CT images from a MicroPET study performed with (S)-[$^{18}$F]4 in a Fisher rat with an intracranial 9L gliosarcoma tumor. The PET portion of this image represents summed data from throughout the 120 min study. The focus of high uptake represents the 9L gliosarcoma tumor.
Figure 13:
FIG. 13 shows fused PET/CT image from a MicroPET study performed with (S)-[$^{18}$F]4 in a Fisher rat with a subcutaneous 9L gliosarcoma tumor. The PET portion of this image represents summed data from throughout the 120 min study. The focus of high uptake in the right flank (left side of image) represents the 9L gliosarcoma tumor. High uptake is also seen in the bladder (inferior aspect of image at midline) and the right renal collecting system (upper left aspect of image).

The distribution of (R)- and (S)-[$^{18}$F]4 in the normal organs and tissues demonstrated the highest uptake in the kidneys followed by the pancreas at all time points. This pattern of biodistribution has been observed with a wide range of radiolabeled amino acids (Langen, K. J., et al., Nucl. Med. Biol. 33: 287-294, 2006; Martarello, L., et al., J. Med. Chem. 45: 2250-2259, 2002; McConathy, J., et al., J. Med. Chem. 45: 2440-2449, 2002; Shoup, T. M., et al., J. Nucl. Med. 40: 331-338, 1999; Jager, P. L., et al., J. Nucl. Med. 42: 432-445, 2001). As in the brain, (S)-[$^{18}$F]4 demonstrated superior properties for tumor imaging outside the brain compared to the (R)-enantiomer. At 60 minutes postinjection of (S)-[$^{18}$F]4, the magnitude of tumor uptake of radioactivity was significantly higher than in the normal organs and tissues ($p<0.01$) except in the kidneys and pancreas. The tumor to normal tissue ratios at 60 min were at least 2:1 with (S)-[$^{18}$F]4 except in the lung and the spleen which demonstrated ratios of 1.3:1 and 1.5:1, respectively. With (R)-[$^{18}$F]4 at 60 min postinjection, the tumor to normal organ tissue ratios were overall lower than with the (S)-enantiomer, particularly in the blood, liver and small intestine. Comparisons of tumor to normal tissue ratios at each time point obtained with (R)- and (S)-[$^{18}$F]4 are depicted in FIG. 7-FIG. 9.

These biodistribution results in conjunction with the cell uptake assays indicate that 1H-1,2,3-triazole substituted amino acids are biologically active and represent a promising class of non-natural amino acids for tumor imaging. To date, substrates for cationic amino acid transport systems have not been evaluated as potential tumor imaging agents. Although (S)-[$^{18}$F]4 was not entirely selective for cationic amino acid transport, the 50-69% inhibition of uptake by L-His, L-Arg and L-Lys are consistent with a substantial component of cationic amino acid transport. The component of system L transport observed with (S)-[$^{18}$F]4 may also play a role in the tumor uptake of this compound given the efficacy of system L substrates for brain tumor imaging. However, tumor to brain ratios observed with (S)-[$^{18}$F]4 are higher than other more selective system L substrates which are typically on the order of 2:1 to 3:1. This difference may be due to the component of cationic amino acid transport. The relatively high uptake in the lung and spleen observed with (S)-[$^{18}$F]4 may also be due to high levels of cationic amino acid transport in these organs.

The (R)- and (S)-enantiomer of [$^{18}$F]4 demonstrated different in vitro transport properties, and the (S)-enantiomer had superior properties for tumor imaging in the 9L gliosarcoma model. This difference may be due to the fact that the position of the 1H-1,2,3-triazole group of (S)-[$^{18}$F]4 corresponds to the configuration of the side chains of natural L-amino acids including L-histidine and L-phenylalanine Example 9

MicroPET Imaging With (S)-[$^{18}$F]4 in Rats With Subcutaneous and Intracranial 9L Gliosarcoma Tumors MicroPET imaging studies were performed in 2 rats implanted with subcutaneous 9L tumors and 1 rat implanted with an intracranial tumor. The subcutaneous implantations were performed as in the biodistribution studies except that the tumors were allowed to grow for 11 days prior to imaging. The intracranial tumor was implanted in the left midcerebrum using a template method as described previously in La Regina, M. C., et al., Lab. Anim. 34: 265-271, 2000, using a total of 5×10$^4$ cells suspended in 5 □L total volume. Anesthesia was achieved with a mixture of 1% isoflurane/oxygen during image acquisition. Computed axial tomography (CT) images were acquired with a MicroCAT II System (ImTek Inc., Knoxville, Tenn.), and PET data were acquired with MicroPET-FOCUS 120 and 220 scanners (Concorde Micro-Systems Knoxville Tenn., USA) for 120 minutes after the intravenous tail vein injection of 0.24 to 0.31 mCi of (S)-[$^{18}$F]4. The PET and CT images were fused and analyzed using an Amira software package (Carlsbad Calif., USA), and time-activity curves were generated using ASIPro PET data analysis software (Concorde MicroSystems, Knoxville Tenn., USA).

The results of the MicroPET studies of the rats with subcutaneously and intracranially implanted 9L gliosarcoma tumors using (S)-[$^{18}$F]4 corroborated the biodistribution studies and confirmed the promising in vivo tumor imaging properties of (S)-[$^{18}$F]4 in this tumor model. The time-activity curves and representative images from these studies are depicted in FIG. 10, FIG. 11, FIG. 12, and FIG. 13, respectively. Near maximal tumor uptake occurred with both the intracranial and subcutaneous tumors at approximately 20 min post injection with maximal uptake at 27.5 min and 32.5 min, respectively. During the remainder of the 2 hour study, the amount of radioactivity in the tumors decreased slowly. In contrast, the uptake in the adjacent normal tissues (brain, paraspinal muscle and spinal column) peaked within 5 min post injection and washed out rapidly. The maximal standard uptake value (SUV) observed with the subcutaneous 9L tumor was 1.6 while the maximal SUV for the intracranial tumor was 1.1. The reason for this difference is unclear but may be due to partial volume effect with uptake in the smaller intracranial tumor being averaged with the very low uptake in the surrounding normal brain.

The tumor to normal tissue ratios measured in the MicroPET studies were in good agreement with the biodistribution studies. The subcutaneous tumor MicroPET uptake ratio was approximately 5.0:1 at 30 min in the paraspinal muscle compared to the biodistribution tumor to muscle ratio of 4.7:1 at 30 min. Similarly, the tumor to bone (spinal column) ratio was 2.5:1 at 30 min in the MicroPET study compared to tumor bone (femur) ratio of 2.3:1 in the biodistribution study at the same time point. Finally, the maximal tumor to brain ratios in the MicroPET study were approximately 9:1 compared to 15:1 in the biodistribution study. Again, this difference between the studies may be due to partial volume effect in the MicroPET study.

REFERENCES

1. Singhal, T, Narayanan, T K, Jain, V, Mukherjee, J; Mantil, J. [$^{11}$C]-L-methionine positron emission tomography in the clinical management of cerebral gliomas. Mol Imaging Biol 2008; 10:1-18.
2. Langen, K J, Hamacher, K, Weckesser, M, Floeth, F, Stoffels, G, Bauer, D, Coenen, H H; Pauleit, D. O-(2-[$^{18}$F]fluoroethyl)-L-tyrosine: uptake mechanisms and clinical applications. Nucl Med Biol 2006; 33: 287-94.
3. Chen, W, Silverman, D H, Delaloye, S, Czernin, J, Kamdar, N, Pope, W, Satyamurthy, N, Schiepers, C; Cloughesy, T. $^{18}$F-FDOPA PET imaging of brain tumors: comparison study with $^{18}$F-FDG PET and evaluation of diagnostic accuracy. J Nucl Med 2006; 47: 904-11.

4. Langen, K J, Pauleit, D; Coenen, H H. 3-[$^{123}$I]-alpha-methyl-L-tyrosine: uptake mechanisms and clinical applications. Nucl Med Biol 2002; 29: 625-31.
5. McConathy, J; Goodman, M M. Non-natural amino acids for tumor imaging using positron emission tomography and single photon emission computed tomography. Cancer Metastasis Rev 2008; 27: 555-73.
6. Becherer, A, Szabo, M, Karanikas, G, Wunderbaldinger, P, Angelberger, P, Raderer, M, Kurtaran, A, Dudczak, R; Kletter, K. Imaging of advanced neuroendocrine tumors with $^{18}$F-FDOPA PET. J Nucl Med 2004; 45: 1161-7.
7. Montravers, F, Grahek, D, Kerrou, K, Ruszniewski, P, de Beco, V, Aide, N, Gutman, F, Grange, J D, Lotz, J P; Talbot, J N. Can fluorodihydroxyphenylalanine PET replace somatostatin receptor scintigraphy in patients with digestive endocrine tumors? J Nucl Med 2006; 47: 1455-62.
8. Schuster, D M, Votaw, J R, Nieh, P T, Yu, W, Nye, J A, Master, V, Bowman, F D, Issa, M M; Goodman, M M. Initial experience with the radiotracer anti-1-amino-3-$^{18}$F-fluorocyclobutane-1-carboxylic acid with PET/CT in prostate carcinoma. J Nucl Med 2007; 48: 56-63.
9. Oka, S, Hattori, R, Kurosaki, F, Toyama, M, Williams, L A, Yu, W, Votaw, J R, Yoshida, Y, Goodman, M M; Ito, O. A preliminary study of anti-1-amino-3-$^{18}$F-fluorocyclobutyl-1-carboxylic acid for the detection of prostate cancer. J Nucl Med 2007; 48: 46-55.
10. Fuchs, B C, Finger, R, Onan, M C; Bode, B P. ASCT2 silencing regulates mammalian target-of-rapamycin growth and survival signaling in human hepatoma cells. Am J Physiol Cell Physiol 2007; 293: C55-63.
11. Fuchs, B C; Bode, B P. Amino acid transporters ASCT2 and LAT1 in cancer: partners in crime? Semin Cancer Biol 2005; 15: 254-66.
12. Esseghir, S, Rcis-Filho, J S, Kennedy, A, James, M, O'Hare, M J, Jeffery, R, Poulsom, R; Isacke, C M. Identification of transmembrane proteins as potential prognostic markers and therapeutic targets in breast cancer by a screen for signal sequence encoding transcripts. J Pathol 2006; 210: 420-30.
13. Nawashiro, H, Otani, N, Shinomiya, N, Fukui, S, Ooigawa, H, Shima, K, Matsuo, H, Kanai, Y; Endou, H. L-type amino acid transporter 1 as a potential molecular target in human astrocytic tumors. Int J Cancer 2006; 119: 484-92.
14. Demko, Z P; Sharpless, K B. An intramolecular [2+3] cycloaddition route to fused 5-heterosubstituted tetrazoles. Org Lett 2001; 3: 4091-4.
15. Mindt, T L, Struthers, H, Brans, L, Anguelov, T, Schweinsberg, C, Maes, V, Tourwe, D; Schibli, R. "Click to chelate": synthesis and installation of metal chelates into biomolecules in a single step. J Am Chem Soc 2006; 128: 15096-7.
16. Glaser, M; Arstad, E. "Click labeling" with 2-[$^{18}$F]fluoroethylazide for positron emission tomography. Bioconjug Chem 2007; 18: 989-93.
17. Martarello, L, McConathy, J, Camp, V M, Malveaux, E J, Simpson, N E, Simpson, C P, Olson, J J, Bowers, G D; Goodman, M M. Synthesis of syn- and anti-1-amino-3-[$^{18}$F]fluoromethyl-cyclobutane-1-carboxylic acid (FMACBC), potential PET ligands for tumor detection. J Med Chem 2002; 45: 2250-9.
18. McConathy, J, Martarello, L, Malveaux, E J, Camp, V M, Simpson, N E, Simpson, C P, Bowers, G D, Olson, J J; Goodman, M M. Radiolabeled amino acids for tumor imaging with PET: radiosynthesis and biological evaluation of 2-amino-3-[$^{18}$F]fluoro-2-methylpropanoic acid and 3-[$^{18}$F]fluoro-2-methyl-2-(methylamino)propanoic acid. J Med Chem 2002; 45: 2240-9.
19. McConathy, J, Martarello, L, Malveaux, E J, Camp, V M, Simpson, N E, Simpson, C P, Bowers, G D, Zhang, Z, Olson, J J; Goodman, M M. Synthesis and evaluation of 2-amino-4-[$^{18}$F]fluoro-2-methylbutanoic acid (FAMB): relationship of amino acid transport to tumor imaging properties of branched fluorinated amino acids. Nucl Med Biol 2003; 30: 477-90.
20. Shoup, T M, Olson, J, Hoffman, J M, Votaw, J, Eshima, D, Eshima, L, Camp, V M, Stabin, M, Votaw, D; Goodman, M M. Synthesis and evaluation of [$^{18}$F]1-amino-3-fluorocyclobutane-1-carboxylic acid to image brain tumors. J Nucl Med 1999; 40: 331-8.
21. Yu, W, McConathy, J, Olson, J, Camp, V M; Goodman, M M. Facile Stereospecific Synthesis and Biological Evaluation of (S)- and (R)-2-Amino-2-methyl-4-[$^{123}$I]iodo-3-(E)-butenoic Acid for Brain Tumor Imaging with Single Photon Emission Computerized Tomography. J Med Chem 2007; 50: 6718-21.
22. Makrides, V, Bauer, R, Weber, W, Wester, H J, Fischer, S, Hinz, R, Huggel, K, Opfermann, tyrosine (D-FET) into the porcine brain. Brain Res 2007; 1147: 25-33.
23. Langen, K J, Hamacher, K, Bauer, D, Broer, S, Pauleit, D, Herzog, H, Floeth, F, Zilles, K; Coenen, H H. Preferred stereoselective transport of the D-isomer of cis-4-[$^{18}$F] fluoro-proline at the blood-brain barrier. J Cereb Blood Flow Metab 2005; 25: 607-16.
24. Gazzola, G C, Dall'Asta, V, Franchi-Gazzola, R; White, M F. The cluster-tray method for rapid measurement of solute fluxes in adherent cultured cells. Anal Biochem 1981; 115: 368-74.
25. La Regina, M C, Culbreth, V O, Higashikubo, R, Roti Roti, J L; Spitz, D R. An alternative method to stereotactic inoculation of transplantable brain tumours in large numbers of rats. Lab Anim 2000; 34: 265-71.
26. Shotwell, M A, Kilberg, M S; Oxender, D L. The regulation of neutral amino acid transport in mammalian cells. Biochim Biophys Acta 1983; 737: 267-84.
27. Christensen, H N, Oxender, D L, Liang, M; Vatz, K A. The use of N-methylation to direct route of mediated transport of amino acids. J Biol Chem 1965; 240: 3609-16.
28. Palacin, M, Estevez, R, Bertran, J; Zorzano, A. Molecular biology of mammalian plasma membrane amino acid transporters. Physiol Rev 1998; 78: 969-1054.
29. Closs, E I, Boissel, J P, Habemieier, A; Rotmann, A. Structure and function of cationic amino acid transporters (CATs). J Membr Biol 2006; 213: 67-77.
30. Closs, E I. Expression, regulation and function of carrier proteins for cationic amino acids. Curr Opin Nephrol Hypertens 2002; 11: 99-107.
31. Jager, P L, Vaalburg, W, Pruim, J, de Vries, E G, Langen, K J; Piers, D A. Radiolabeled amino acids: basic aspects and clinical applications in oncology. J Nucl Med 2001; 42: 432-45.

All publications, patents, patent applications, and other references cited in this application are incorporated herein by reference in their entirety. Citation of a reference herein shall not be construed as an admission that such is prior art relevant to patentability of the present invention.

What is claimed is:

1. A 1H-[1,2,3]triazole substituted amino acid of structure

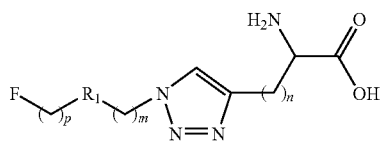

wherein $R_1$ is $CH_2$ or O, n is an integer from 0 to 3, m is an integer from 0 to 1, and p is an integer from 0 to 1 wherein F is $^{18}F$.

2. A 1H-[1,2,3]triazole substituted amino acid in accordance with claim 1, wherein $R_1$ is $CH_2$, n is from 1 to 3, m is 0, p is 1, and F is an $^{18}F$.

3. A 1H-[1,2,3]triazole substituted amino acid in accordance with claim 1, wherein $R_1$ is $CH_2$, n is 1, m is 0, p is 1, and F is an $^{18}F$.

4. A 1H-[1,2,3]triazole substituted amino acid in accordance with claim 1, wherein $R_1$ is $CH_2$, n is 2, m is 0, p is 1, and F is an $^{18}F$.

5. A 1H-[1,2,3]triazole substituted amino acid in accordance with claim 1, wherein $R_1$ is $CH_2$, n is 3, m is 0, p is 1, and F is an $^{18}F$.

6. A 1H-[1,2,3]triazole substituted amino acid or salt thereof in accordance with claim 1, wherein the acid is selected from the group consisting of

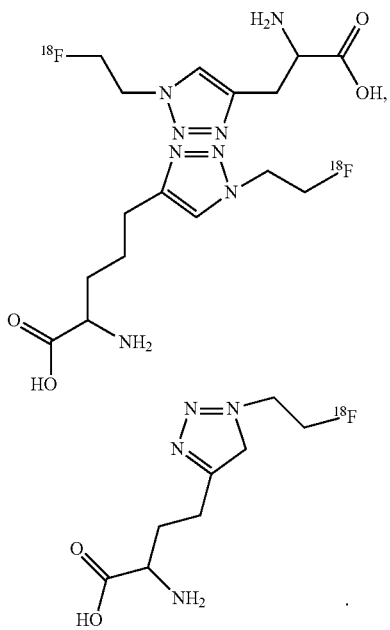

7. A 1H-[1,2,3]triazole substituted amino acid of structure

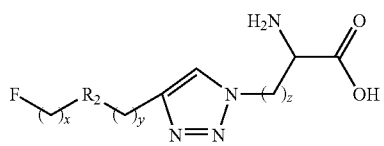

wherein $R_2$ is $CH_2$ or O, z is an integer from 0 to 3, y is an integer from 0 to 1, and x is an integer from 0 to 2 wherein F is $^{18}F$.

8. A 1H-[1,2,3]triazole substituted amino acid in accordance with claim 7, wherein $R_2$ is O, z is 1 to 3, y is 1, x is 2, and the F is an $^{18}F$.

9. A 1H-[1,2,3]triazole substituted amino acid in accordance with claim 7, wherein $R_2$ is O, z is 1, y is 1, x is 2, and the F is an $^{18}F$.

10. A 1H-[1,2,3]triazole substituted amino acid in accordance with claim 7, wherein $R_2$ is O, z is 2, y is 1, x is 2, and the F is an $^{18}F$.

11. A 1H-[1,2,3]triazole substituted amino acid in accordance with claim 7, wherein $R_2$ is O, z is 3, y is 1, x is 2, and the F is an $^{18}F$.

12. A 1H-[1,2,3]triazole substituted amino acid in accordance with claim 7, wherein the acid is selected from the group consisting of

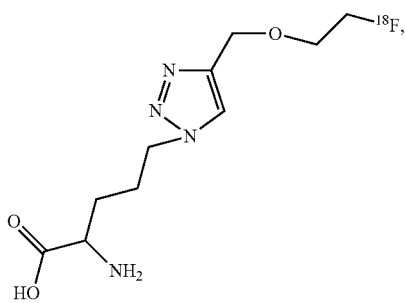

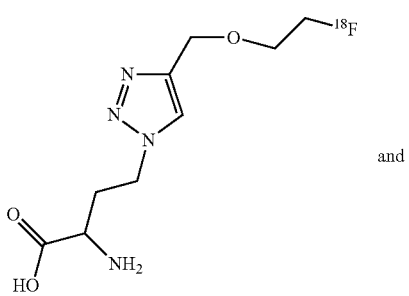

13. A method of imaging a tumor in a mammal, the method comprising:

administering to the mammal a 1H-[1,2,3]triazole substituted amino acid of claim 1; and subjecting the mammal to PET scanning.

14. A method of imaging a tumor in a mammal in accordance with claim 13, wherein the 1H-[1,2,3]triazole substituted amino acid is selected from the group consisting of
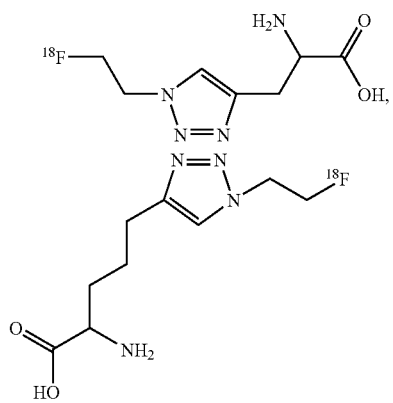
and
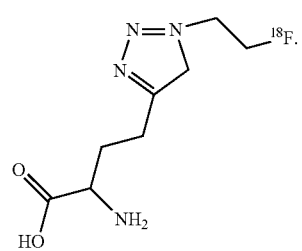
15. A method of imaging a tumor in a mammal in accordance with claim 13, wherein the 1H-[1,2,3]triazole substituted amino acid is selected from the group consisting of
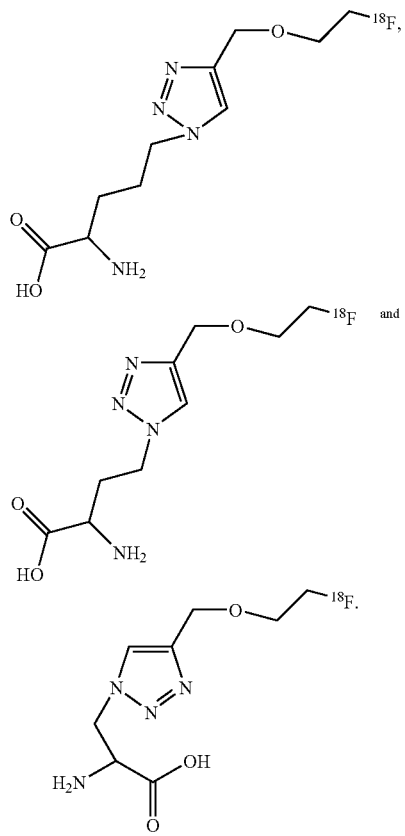
* * * * *